(12) United States Patent
Clark et al.

(10) Patent No.: US 7,875,247 B2
(45) Date of Patent: Jan. 25, 2011

(54) UV FLUX MULTIPLICATION SYSTEM FOR STERILIZING AIR, MEDICAL DEVICES AND OTHER MATERIALS

(75) Inventors: Reginald W. Clark, San Diego, CA (US); Bernard J. Eastlund, San Diego, CA (US); Michael W. Ingram, San Diego, CA (US); Joseph C. Stumpf, Carlsbad, CA (US)

(73) Assignee: Novatron, Inc., San Diego, CA (US)

( * ) Notice: Subject to any disclaimer, the term of this patent is extended or adjusted under 35 U.S.C. 154(b) by 837 days.

(21) Appl. No.: 11/781,812

(22) Filed: Jul. 23, 2007

(65) Prior Publication Data
US 2008/0152548 A1 Jun. 26, 2008

Related U.S. Application Data

(63) Continuation-in-part of application No. 10/724,017, filed on Nov. 26, 2003, now abandoned.

(60) Provisional application No. 60/429,880, filed on Nov. 27, 2002, provisional application No. 60/471,485, filed on May 15, 2003, provisional application No. 60/486,849, filed on Jul. 10, 2003, provisional application No. 60/495,500, filed on Aug. 14, 2003, provisional application No. 60/496,195, filed on Aug. 18, 2003.

(51) Int. Cl.
*A61L 9/20* (2006.01)
(52) U.S. Cl. .................. 422/121; 422/24; 422/120; 250/455.11
(58) Field of Classification Search ............ 422/24, 422/186.3, 292, 120, 121; 250/455.11
See application file for complete search history.

(56) References Cited

U.S. PATENT DOCUMENTS 4,035,085 A 7/1977 Seiner (Continued)

FOREIGN PATENT DOCUMENTS

WO WO 99/22777 5/1999

(Continued)

OTHER PUBLICATIONS

Beverly, III R.E., *Characterization of a dual-segment cylindrical surface discharge*, J. Appl. Phys. 69(7), Apr. 1991.

(Continued)

*Primary Examiner*—Sean E Conley
(74) *Attorney, Agent, or Firm*—Knobbe Martens Olson & Bear LLP

(57) ABSTRACT

An ultraviolet flux multiplying air sterilization chamber comprises inner surfaces having a diffuse reflective behavior. The sterilization chamber includes an inlet aperture and an outlet aperture for air to flow through said chamber and a light source emitting an ultraviolet light. Due to the reflectivity of the inner surfaces of the chamber, a flux of the ultraviolet light is multiplied by reflecting multiple times from the inner surfaces of the chamber. The inlet and outlet apertures are advantageously configured to reduce the amount of light that escapes from the chamber and increase the amount of photons available in the chamber. In an exemplary embodiment, perforated end panels having diffuse, reflective interior surfaces may be provided over at least a portion of the inlet and outlet apertures.

27 Claims, 28 Drawing Sheets

U.S. PATENT DOCUMENTS

| | | | |
|---|---|---|---|
| 4,687,579 | A | 8/1987 | Bergman |
| 5,112,370 | A | 5/1992 | Gazzano |
| 5,462,705 | A | 10/1995 | Springsteen |
| 5,596,450 | A | 1/1997 | Hannon et al. |
| 5,612,001 | A | 3/1997 | Matschke |
| 5,656,242 | A * | 8/1997 | Morrow et al. ............... 96/224 |
| 5,689,364 | A | 11/1997 | McGregor et al. |
| 5,891,399 | A * | 4/1999 | Owesen ..................... 422/121 |
| 6,022,511 | A | 2/2000 | Matschke |
| 6,228,327 | B1 | 5/2001 | Matschke |
| 6,500,387 | B1 | 12/2002 | Bigelow |
| 6,589,489 | B2 | 7/2003 | Morrow et al. |
| 6,730,141 | B2 | 5/2004 | Goebel et al. |
| 6,911,186 | B2 * | 6/2005 | Taylor et al. .......... 422/186.07 |
| 6,955,708 | B1 * | 10/2005 | Julos et al. .................... 95/59 |
| 2002/0098127 | A1 | 7/2002 | Bollini |
| 2005/0163648 | A1 | 7/2005 | Liang |

FOREIGN PATENT DOCUMENTS

WO    WO 2004/050130    6/2004

OTHER PUBLICATIONS

Beverly, III, R.E., *Electrical Gasdynamic, and Radiative Properties of Planar Surface Discharges*, J. Appl. Phys. 60(1), Jul. 1986.

Pasikatan, et al., *Review: Near Infrared Reflectance Spectroscopy for Online Particle Size Analysis of Powders and Ground Materials*, J. Near Infrared Spectrosc. 9:153-164 (2001).

VanOsdell, et al., *Defining the Effectiveness of UV Lamps Installed in Circulating Air Ductwork*, RTI International, Nov. 2002.

Wick, et al., *Pulsed Light Device (PLD) for Deactivation of Biological Aerosols*, Edgewood Report ERDC-TR-456, Dec. 1998.

Allegra, et al., *A Novel Device for the Prevention of Airborne Infections*, J. Clinical Microbiology Letters to the Editor, 35(7):1918-1919, Jul. 1997.

Jensen, M., *Inactivation of Airborne Viruses by Ultraviolet Irradiation*, Applied Microbiology, 12(5):418-420, Sep. 1964.

* cited by examiner

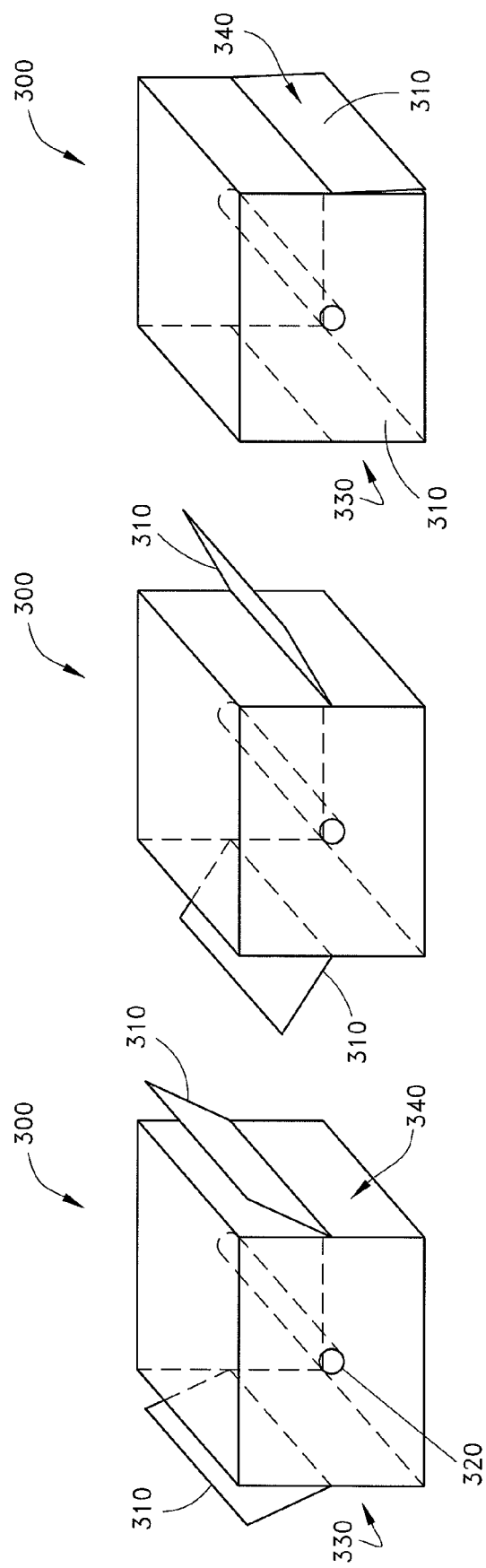

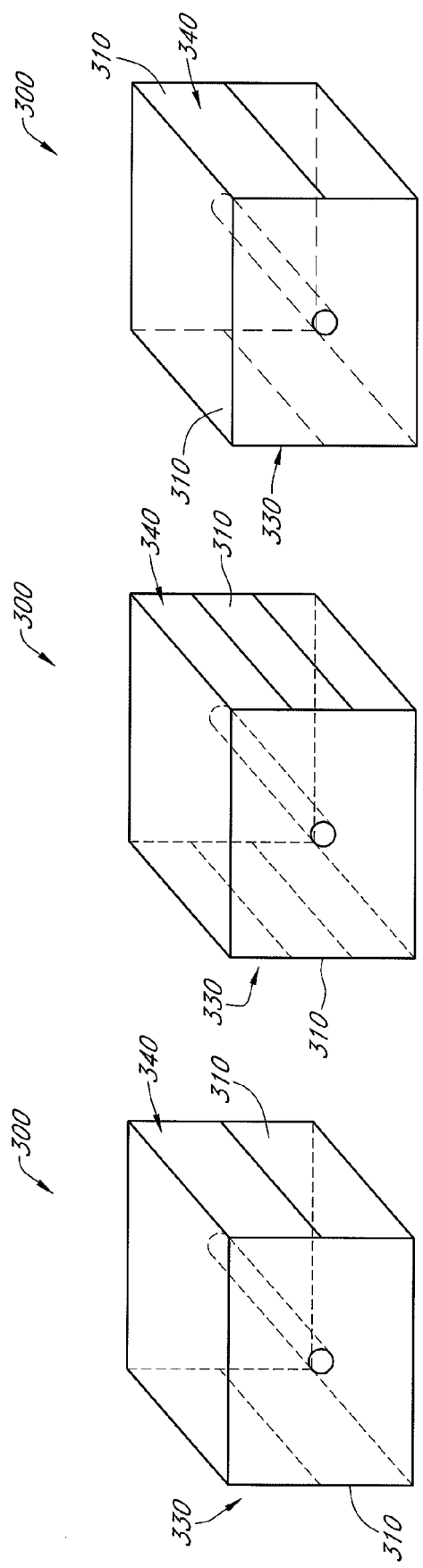

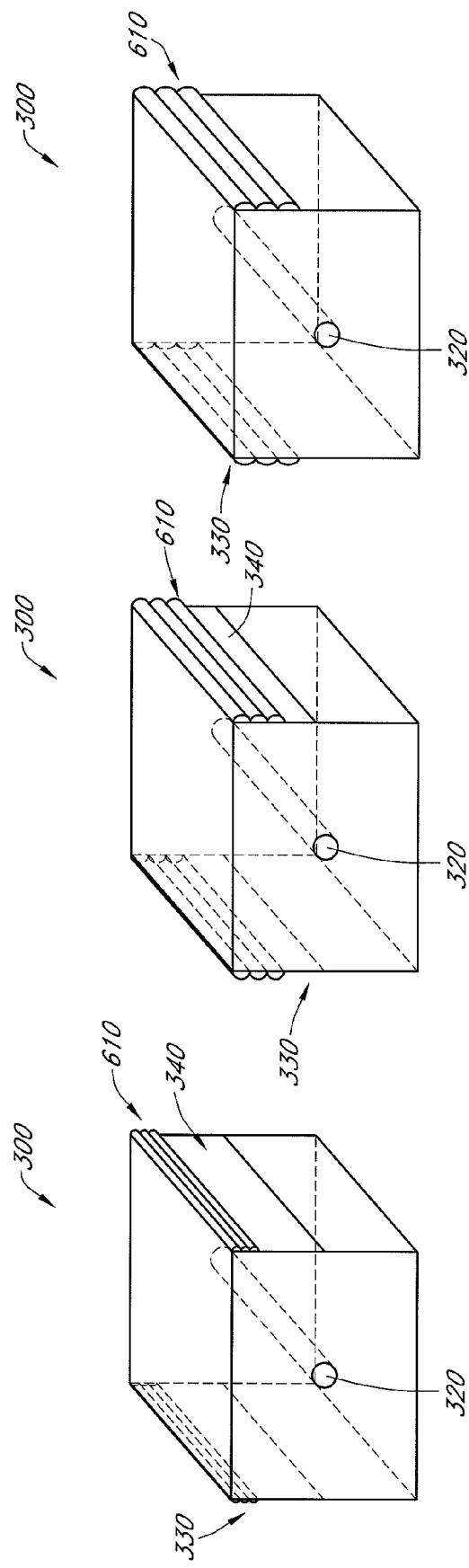

UV FLUX MULTIPLICATION SYSTEM FOR STERILIZING AIR, MEDICAL DEVICES AND OTHER MATERIALS

RELATED APPLICATION

This application is a continuation-in-part of U.S. application Ser. No. 10/724,017, filed Nov. 26, 2003, now published as U.S. Publication No. 2004/0166018 A1, which claims the benefit of U.S. Provisional Application No. 60/429,880, filed Nov. 27, 2002, U.S. Provisional Application No. 60/471,485, filed May 15, 2003, U.S. Provisional Application No. 60/486,849, filed Jul. 10, 2003, Provisional Application No. 60/495,500, filed Aug. 14, 2003 and Provisional Application No. 60/496,195, filed Aug. 18, 2003, the disclosures of each of which are hereby incorporated by reference.

GOVERNMENT RIGHTS

The invention was made with government support and the government has certain rights in the invention.

BACKGROUND OF THE INVENTION

1. Field of the Invention

This invention relates to a sterilization system that may be used for sterilizing air in HVAC systems and for other applications requiring high flux of UV light.

2. Description of the Related Art

Air sterilization systems attempt to remove or kill harmful microorganisms that may exist in the air. Because ultraviolet radiation can kill a broad range of harmful microorganisms, one method of sterilizing air is through the use of ultraviolet (UV) lamps. Continuous wave UV light (CWUV) has been proposed for sanitation of air in Heating, Ventilation, & Air Conditioning (HVAC) systems. For example, U.S. Pat. No. 6,022,511 issued to Matschke discloses a sterilization system that replaces one or more sections of air ducts with ellipsoidal ducts containing ultraviolet light sources and having parabolic or ellipsoidal reflectors disposed in an inlet and an outlet for flow of air.

Pulsed flash lamps have been shown to sterilize flowing air in ducts. For example, Wick, C. H. et al, "Pulsed Light Device for Deactivation of Biological Aerosols," Edgewood Report ERDC-TR-456, December, 1968 shows that pulsed light sources can kill 99.999% of *B. thuringiensis* spores at a flow rate of 200 cubic feet per minute.

Conventional sterilization chambers are often unable to provide the desired kill rate for bacteria and microorganisms. In particular, for cases of high air flow velocity, CWUV based systems need to be up to 200 feet long to produce 99.9999% kill of spores. Accordingly, there is a need for sterilization chambers that are configurable to be used in existing HVAC system and that reduce the power requirements necessary to provide a desired kill.

SUMMARY OF THE INVENTION

The invention described herein provides for a reduction in power requirements of a factor of over 100 compare to the Wick et al results. In one example, it is shown that the power required to kill spores to a level of 99.9999% is on the order of 1,500 watts, at a flow rate of 10,000 cubic feet per minute (cfm.), or about the same as the requirement for a hand held hair dryer. The inventions also decrease the number of lamps required for air duct sterilization with pulsed flash lamps or CWUV lamps. The invention also decreases the size of the air duct sterilization systems, making them easier to retrofit into buildings. The invention allows flexibility in locating the light sources within the chamber.

When reflectors restrict the flow of air they create a pressure drop in the flow which increases power consumption. The openings for flow also reduce effectiveness by allowing light to escape from the irradiation chamber. The use of optically reflective (specular) surfaces also limit the effectiveness of homogeneously distributing photons within the irradiation chamber. Thus, one aspect of the invention is to provide an air sterilization chamber that reduces the amount of light that escapes from the chamber and increases the amount of photons available in the chamber, while minimizing the pressure drop created.

In one embodiment, the invention comprises a UV flux multiplying light trap. One application of the invention is an air sterilization chamber with an inlet and outlet for flowing air. The UV flux multiplying light trap is designed so that the ratio of the sum of all areas (e.g. light leaking) and light absorbing areas, including lamps, to the total area of the chamber is less than about 10%. When this criterion is satisfied, and the reflectivity of all other surfaces is Lambertian and greater than about 90%, the chamber acts as a UV flux multiplier and increases the UV flux from a UV source by factors of between 5 and 100. A key factor in achieving these conditions in air flowing in an air duct is to design inlets and outlets to the chamber that allow a low pressure drop in the flowing air, while reflecting about 75% or more of the incident UV light. Embodiments described below include various approaches to allowing highly reflective inlets and outlets with low pressure drop for the flowing air.

In one embodiment, a flux multiplying method and system is described. An application of the invention is an air sterilization chamber with an inlet and outlet for flowing air that is filled with light of UV, optical and/or IR wavelengths wherein the light is confined within the chamber by highly reflective surfaces with reflectivity greater than 75% and wherein individual light photons pass through the chamber many (e.g 5-100) times providing a high probability for interaction with biological organisms or chemicals disposed within the chamber. The light can be disposed within the chamber or shine into the chamber through a lamp aperture.

In one embodiment, a flux multiplying light trap comprises an apparatus with no moving parts that traps light with highly reflective walls and highly reflective inlets and outlets that allow a low pressure drop of flowing air while reflecting at least 75% of the incident UV light. The inlet and outlet panels use packed arrays of fibers, spheres, or other small particles to provide many light scattering events such that the light incident on the packed array reflects back with high reflectivity, while the openness of the particle containment structure allows air flow with low pressure drop.

In another embodiment, an air sterilization chamber comprises a pulsed light or a steady state continuous light source disposed within the chamber or shining from outside the chamber, and is configured with an inlet aperture with slats which partially blocks the flow of air into the chamber while reflecting light back into the chamber and an outlet aperture with slats which partially blocks the flow of air out of the chamber while reflecting light back into the chamber, the combination of which enhances multiple reflections of light within the chamber. The chamber apparatus may be of arbitrary shape, including parallelepiped.

In another embodiment, chevrons are placed behind the openings in the slats to decrease the velocity of the air acceleration by the openings between the slats. The air can also be slowed by changing the shape of the slats.

In another embodiment, an air sterilization chamber comprises a pulsed light source disposed inside the chamber or shining into the chamber, an inlet aperture for air to flow into the chamber, and an outlet aperture for air to flow out of the chamber. At least one moveable device is attached to the inlet aperture with at least one surface that is highly reflective and where motion is timed to increase the fraction of chamber surface area that is reflective within the chamber when the pulsed light is emitting light. At least one moveable device is attached to the outlet aperture with at least one surface that is highly reflective and where motion is timed to increase the fraction of chamber interior surface area that is reflective within the chamber when the pulsed light source is emitting light. The motion of the inlet and outlet devices would be synchronized to occur at the same time.

In another embodiment, an air sterilization chamber comprises a pulsed light source disposed within the chamber or shining from outside the chamber, and at least one moveable mechanism to increase the fraction of chamber interior surface area that is reflective. The moveable mechanism may comprise a flap (or flaps) configured to cover the inlet aperture and a flap (or flaps) configured to cover the outlet aperture when the light source is emitting light and to be removed from the inlet and the outlet aperture when the light source is not emitting light. The flaps comprise a highly reflective surface on at least the side facing the interior of the chamber and the motion of the inlet and outlet flaps is synchronized. The moveable mechanism may also comprise a flat surface that is covered with a highly reflective material and slides parallel to an outer surface of the chamber to cover the inlet and outlet apertures with a reflective surface and when the pulsed light is emitting light and are open when the pulsed light source is not emitting light. The moveable mechanism may also comprise a venetian blind configuration with reflective surfaces on the side of the slats that face the interior of the chamber when the pulsed light source is emitting light and are open when the pulsed light source is not emitting light. The moveable mechanism may also comprise a rotating drum configuration located at each of the inlet and outlet apertures wherein a rotating drum has a plurality of retractable vanes extending from a peripheral surface of the rotating drum. The rotating drum configuration reflects light into the interior of the chamber at all times and does not require synchronization of the inlet and outlet units.

In another embodiment, an air sterilization chamber comprises a steady state, continuously operating light source disposed within the chamber or shining from the outside of the chamber, comprise a rotating drum configuration located at each of the inlet and outlet apertures wherein a rotating drum has a plurality of retractable vanes extending from a peripheral surface of the rotating drum. The rotating drum configuration reflects light into the interior of the chamber at all times. The rotating drum configuration comprises a housing and a rotating drum mounted on an axle within the housing, the rotating drum having highly reflective outer surfaces and a plurality of moveable vanes on the periphery of the rotating drum, wherein the vanes are each respectively extended during a first portion of the rotation of the drum and the plurality of vanes are each respectively retracted during a second portion of the rotation of the drum. When the rotating drum mechanism is located at the inlet aperture of the sterilization chamber, a particular vane is extended and the particular vane may force air in to the sterilization chamber. When the vane is retracted it does not affect the air flow and avoids forcing air back against the incoming air, which would result in no net motion of the drum. The rotating drum mechanism may be rotated by a variety of external energy sources, such as a motor that turns the drum, a pneumatic source that blow air on the vanes in order to rotate the drum, or the drum may freewheel due to the force of the flowing air inside the duct where the sterilization chamber is mounted. When the rotating drum mechanism is located at the outlet aperture, a particular vane, when extended, may force air out of the sterilization chamber, providing continuity of flow through the duct.

In another embodiment, the effectiveness of the reflective surfaces to fill the sterilization chamber homogeneously with light is enhanced by utilizing reflective surfaces that are highly reflective, with reflectivity greater than 75% and also with diffuse reflecting surfaces rather than specular reflecting surfaces. In another embodiment the reflecting surfaces can be composed of PTFE, ePTFE or a mixture of a binder and reflecting additives such as barium sulfate, magnesium fluoride, magnesium oxide or aluminum oxide, holmium oxide, calcium oxide, lanthanum oxide, germanium oxide, tellurium oxide, europium oxide, erbium oxide, neodymium oxide, samarium oxide or ytterbium oxide.

In another embodiment, a modular chamber for germicidal cleansing of air configured to interconnect with a plurality of modular chambers comprises a plurality of walls having inner surfaces, wherein each of the inner surfaces may comprise an ultraviolet reflective material having a diffuse reflectivity of greater than about 75%, a first end wall of the plurality of walls having an opening configured to allow air to enter the modular chamber, a second end wall of the plurality of walls disposed opposite the first end wall and having an opening configured to allow air to exit the modular chamber, an ultraviolet light source disposed inside the modular chamber. A first of the plurality of walls may be removably connected to certain of the plurality of walls. The second end wall of the modular chamber may be operably coupled to a third end wall of a second modular chamber so that substantially all of the air exiting the opening through the second end wall enters an opening in the third end wall. The first end wall of the modular chamber may be operably coupled to a fourth end wall of a third modular chamber so that substantially all of the air entering the opening through the first end wall exits an opening in the fourth end wall.

These and other objects and features of the present invention will become more fully apparent from the following description and appended claims taken in conjunction with the following drawings, where like reference numbers indicate identical or functionally similar elements.

BRIEF DESCRIPTION OF THE DRAWINGS

FIG. 12a is a perspective view of the air sterilization chamber of FIG. 11 with the end flaps open.

FIG. 12b is a perspective view of the air sterilization chamber of FIG. 11 with the end flaps partially closed.

FIG. 12c is a perspective view of the air sterilization chamber of FIG. 11 with the end flaps closed.

FIG. 13a is a perspective view of another embodiment of an air sterilization chamber with sliding end flaps with the flaps open.

FIG. 13b is a perspective view of an embodiment of an air sterilization chamber with sliding end flaps with the flaps partially closed.

FIG. 13c is a perspective view of an embodiment of an air sterilization chamber with sliding end flaps with the flaps closed.

FIG. 14a is a perspective view of another embodiment of an air sterilization chamber in which the moveable ends comprise blinds, where the blinds are in the open position.

FIG. 14b is a perspective view of an embodiment of an air sterilization chamber in which the moveable ends comprise blinds, where the blinds are in the partially closed position.

FIG. 14c is a perspective view an embodiment of an air sterilization chamber in which the moveable ends comprise blinds, where the blinds are in the closed position.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the invention herein described.

Embodiments of the invention described herein provide for a reduction in power requirements of a factor of over 100 compared to the Wick et al results. In one example, it is shown that the power required to kill spores to a level of 99.9999% is on the order of 1,500 watts, at a flow rate of 10,000 cubic feet per minute (cfm.), or about the same as the requirement for a hand held hair dryer. The inventions also decrease the number of lamps required for air duct sterilization with pulsed flash lamps or CWUV lamps. The invention also decreases the size of the air duct sterilization systems, making them easier to retrofit into buildings. The invention allows flexibility in locating the light sources within the chamber.

Several embodiments of sterilization chambers will be discussed in detail below, each embodiment having certain similar advantages and certain different advantages. For example, advantageous embodiments include inner surfaces that reflect the light from a sterilization lamp in order to make better use of the lamp's irradiation. Several embodiments having various air inlet and outlet mechanism are described also. Each embodiment is configured to decrease an amount of light that escapes from the sterilization chamber, while allowing air to flow through the chamber at an efficient rate. The various sterilization chamber embodiments described herein may be implemented in a modular fashion. The sterilization techniques may be applied to a duct in an HVAC system.

Existing sterilization systems typically require a specific chamber geometry in order to reflect incident light to provide uniform illumination within the volume of the chamber. For example, when a chamber is covered with a substantially specular reflector, such as spun aluminum, reflected light will only pass through those points within the chamber that lie on a line coincident with the angle of reflection which is equal to the angle of incidence. Thus, in order to provide uniform illumination, a specific geometry, such as the ellipsoid used in Matschke, is manufactured and carefully constructed so as to distribute the energy uniformly throughout the chamber. However, if the inner surfaces of a chamber comprise a diffuse reflector having a high reflectivity, the geometry of the chamber becomes less constrained.

Figure 1A:
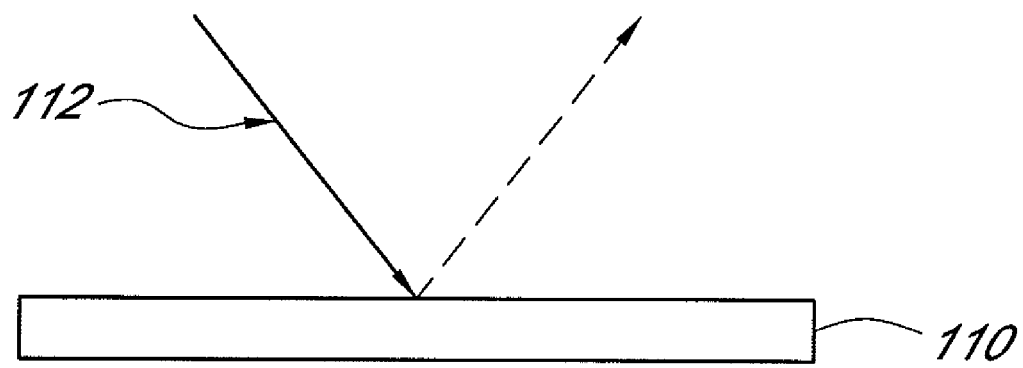
FIG. 1A is a diagram illustrating light reflected from a specular reflector.
Figure 1B:
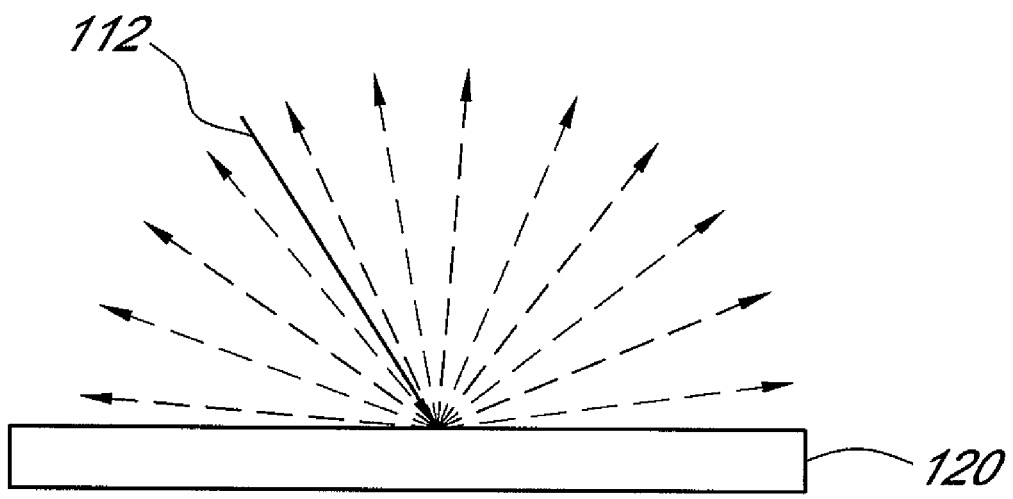
FIG. 1B is a diagram illustrating light reflected from a diffuse reflector.

FIG. 1A is a diagram illustrating light reflected from a specular reflector 110 and FIG. 1B is a diagram illustrating light reflected from a diffuse reflector 120. In FIGS. 1A and 1B, the incident light is represented as solid lines and reflected light is represented as dashed lines. As shown in FIG. 1A, the specular reflector 110 reflects an incident light 112 predominantly in one direction, which is determined by the angle of incidence. One example of a specular reflector is a mirror in which the angle of incidence and the angle of reflection are substantially identical.

Figure 6:
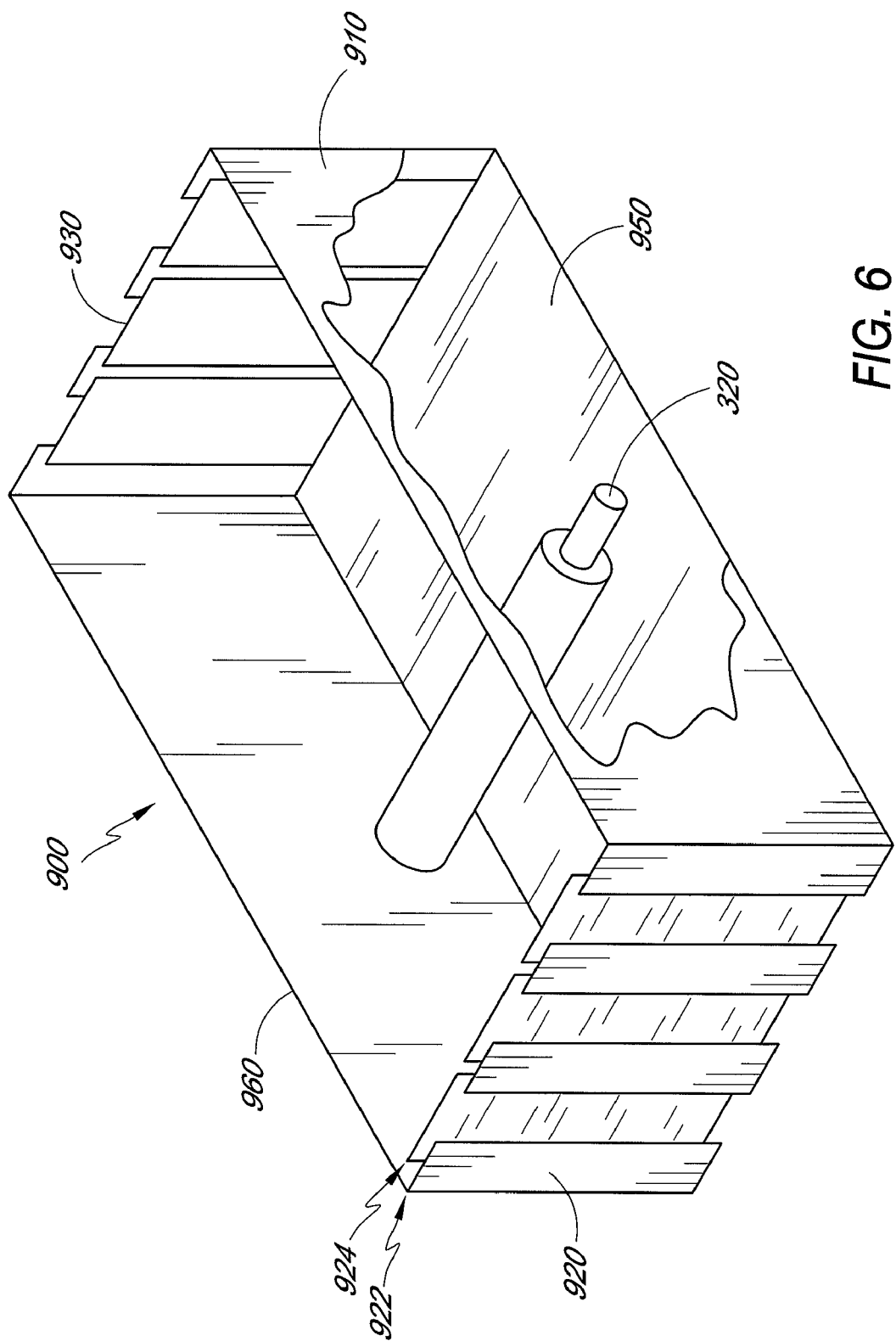
FIG. 6 is a perspective view of an embodiment of an air sterilization chamber with slats.

Conversely, the diffuse reflector 120 reflects the incident light 112 in all directions regardless of the angle it is incident on the diffuse reflector 120. A diffuse reflecting surface is typically referred to as Lambertian. A Lambertian surface is defined as a surface from which the energy emitted in any direction is proportional to the cosine of the angle which that direction makes with the normal to the surface. For example, if diffuse reflector 120 represents a portion of a panel in sterilization chamber, incident light 112 will be scattered from the panel in all directions regardless of the shape of the diffuse reflector 120 and the relationship of other panels in the sterilization chamber. By making the surfaces of the sterilization chamber highly diffusely reflective, the fluence within the chamber may be made substantially uniform regardless of the chamber geometry (e.g. the parallelepiped sterilization chamber 900), UV source geometry, and UV source location within the chamber (e.g. coupled between the front and rear panels as in FIG. 6). Thus, a substantially uniform illumination inside the sterilization chamber is possible regardless of the geometric shape of the chamber and the location of the emitter within the chamber.

In one embodiment, the emitter may be any source of UV, such as a flashlamp or a pulsed lamp, which provides broad spectrum pulsed light and can be purchased through vendors such as Fenix, of Yuma, Ariz., medium pressure mercury arcs, available from Hanovia Corp, and germicidal lamps. In one embodiment, the highly diffuse reflective material may comprise one or more of: Spectralon™ which has a reflectivity of about 94%, ODM, manufactured by Gigahertz-optik, which has a reflectivity of 95%, and DRP which has a reflectivity of 99.4 to 99.9%. Spectralon™, which is a highly Lambertian, thermoplastic material that can be machined into a wide variety of shapes to suit various reflectance component requirements, may be purchased from Labsphere, Inc. DRP can be purchased in sheet form, with a peel and stick backing from W. L. Gore and Associates. In another embodiment, the highly reflective material comprises an Alzak oxidized aluminum, which has a reflectivity of about 86%.

Analysis of the flux distribution in a chamber can require the use of complex computer simulations which consider the detailed position of lamps in the duct and count direct rays as well as multiply reflected rays. Multiple reflections of reflected rays dominate the distribution of light within the chamber when the reflectivity rises above about 75%, and the distribution of light may be analyzed using formulas similar to those well developed for "integrating sphere" applications.

The amount of energy required for an air sterilization chamber to achieve a predetermined kill rate is a function of the reflectivity of the inner surfaces of the sterilization chamber, the amount of open area and the amount of light absorbing area (e.g. the UV emitter 320). More particularly, as the reflectivity of the inner surfaces increases, the energy required to achieve a specific kill rate decreases, and, likewise, as the open area or the light absorbing area within the chamber decreases the energy required to achieve a specific kill rate decreases. For example, the total light energy $E_{total}$, in joules, required to achieve a particular kill level may be estimated by:

$$E_{total} = \frac{A * F_{kill}}{2M} \quad \text{Equation 1}$$

where $F_{kill}$ is the total fluence in joules/cm² required to achieve a specific kill level, A is the total surface are of the inner surface of the sterilization chamber in cm² and M is a multiplier defined in Equation 2

$$M = \frac{R}{(1 - R(1 - \alpha))} \quad \text{Equation 2}$$

In Equation 2, R is the reflectivity of the inner surface of the sterilization chamber and $\alpha$ is the ratio of the sum of the open areas through which light can escape the chamber and light absorbing areas of the chamber, such as lamp terminals, to the total surface area of the chamber A, and M is the multiplier representing the flux density within the sterilization chamber. As indicated in Equation 2, as $\alpha$ increases the value of M decreases and the corresponding value of $E_{total}$ (Equation 1) increases, indicating a higher required energy for the system to achieve the desired kill rate. Conversely, as R increases the value of M also increases and the corresponding value of $E_{total}$ decreases, indicating a lower required energy for the system to achieve the desired kill rate. As such, in an advantageous embodiment, $\alpha$ is minimized (by decreasing the ratio of open area and light absorbing areas to the total area) and R is maximized (by selecting a material for the inner surfaces of the sterilization chamber with a higher reflectivity) in order to minimize $E_{total}$.

According to one embodiment, the pulse repetition rate of the pulsed lamp is inversely proportional to the length of the sterilization chamber and the maximum air velocity distribution through the sterilization chamber, as shown in Equation 3, where f is the repetition rate in seconds$^{-1}$, $L_O$ is the length of the chamber exposed to the ultraviolet light in feet, and $v_{max}$ is the maximum velocity of air flow in feet per second.

$$f = \frac{v_{max}}{L_O} \quad \text{Equation 3}$$

Thus, as the velocity of air flow $v_{max}$ increases, the required repetition rate f necessary to maintain the same kill rate must be increased. Likewise, as the length of the chamber $L_O$ increases, the required repetition rate f necessary to maintain the same kill rate may be decreased.

Finally, the average power required by the sterilization chamber is estimated by Equation 4, where $E_{total}$ is the total energy as defined in Equation 1 and f is the repetition rate as defined in Equation 3.

$$P_{average} = E_{total} * f \quad \text{Equation 4}$$

Thus, as either the total energy $E_{total}$ or the repetition rate f increase, the average power required also increases.

EXAMPLE 1

Parallelepiped Sterilization Chamber with Moveable Flaps at the Inlet and Exit Ends using a Pulsed Light Source with 30% of Total Fluence Between 200-300 nm

| | |
|---|---|
| Air flow rate (cubic meters/second) | Q = 1,141,600 cm³/sec |
| Average air flow velocity | $V_{ave}$ = 274.3 cm/sec |
| Peak air flow velocity | $v_{max}$ = 362.7 cm/sec |
| Dimensions of chamber | H = 50.8 cm |
| | W = 101.6 cm |
| | L = 304.8 cm |
| Total inner surface area | A = 103,225 cm² |
| Area of Ends | $A_E$ = 10,320 cm² |
| Percentage of ends open to flow | $P_{OE}$ = 2% |
| Open area of Ends | $A_{OE}$ = 206 cm² |
| Number of lamps | $N_L$ = 1 |
| Lamp absorbing area (per lamp) | $A_L$ = 180 cm² |
| Total lamp Area ($N_L \times A_L$) | $A_{TL}$ = 180 cm² |
| Non-reflective area ($A_{OE} + A_{TL}$) | $A_O$ = 386 cm² |
| Ratio of non-reflecting area to total area ($A_O$/A) | α = 0.0037 |
| Reflectivity | R = 99% |
| Fluence required for kill (99.9999%) | $F_{kill}$ = 0.6 Joule/cm² |

Given the above parameters and performance criteria of the exemplary sterilization chamber, Equations 1 and 2 may be utilized to determine the total energy required to achieve the prescribed fluence $F_{kill}$ required for the desired kill rate. First, the multiplier M may be determined using Equation 2. Specifically, according to Equation 2, $$M = \frac{R}{(1 - R(1 - \alpha))}. \text{ Thus, } M = \frac{.99}{(1 - .99(1 - .0037))} = 72.$$

With the multiplier M calculated, total optical energy $E_{total}$ required to achieve a particular kill level may be determined using Equation 1. Specifically, according to Equation 1, $$E_{total} = \frac{A * F_{kill}}{2M}. \text{ Thus, } E_{total} = \frac{103,225 * .6}{2(72)} = 430 \text{ joules.}$$

Equation 3 may be used to determine the required repetition rate f. According to Equation 3, $$f = \frac{v_{max}}{L_O}.$$

Figure 2:
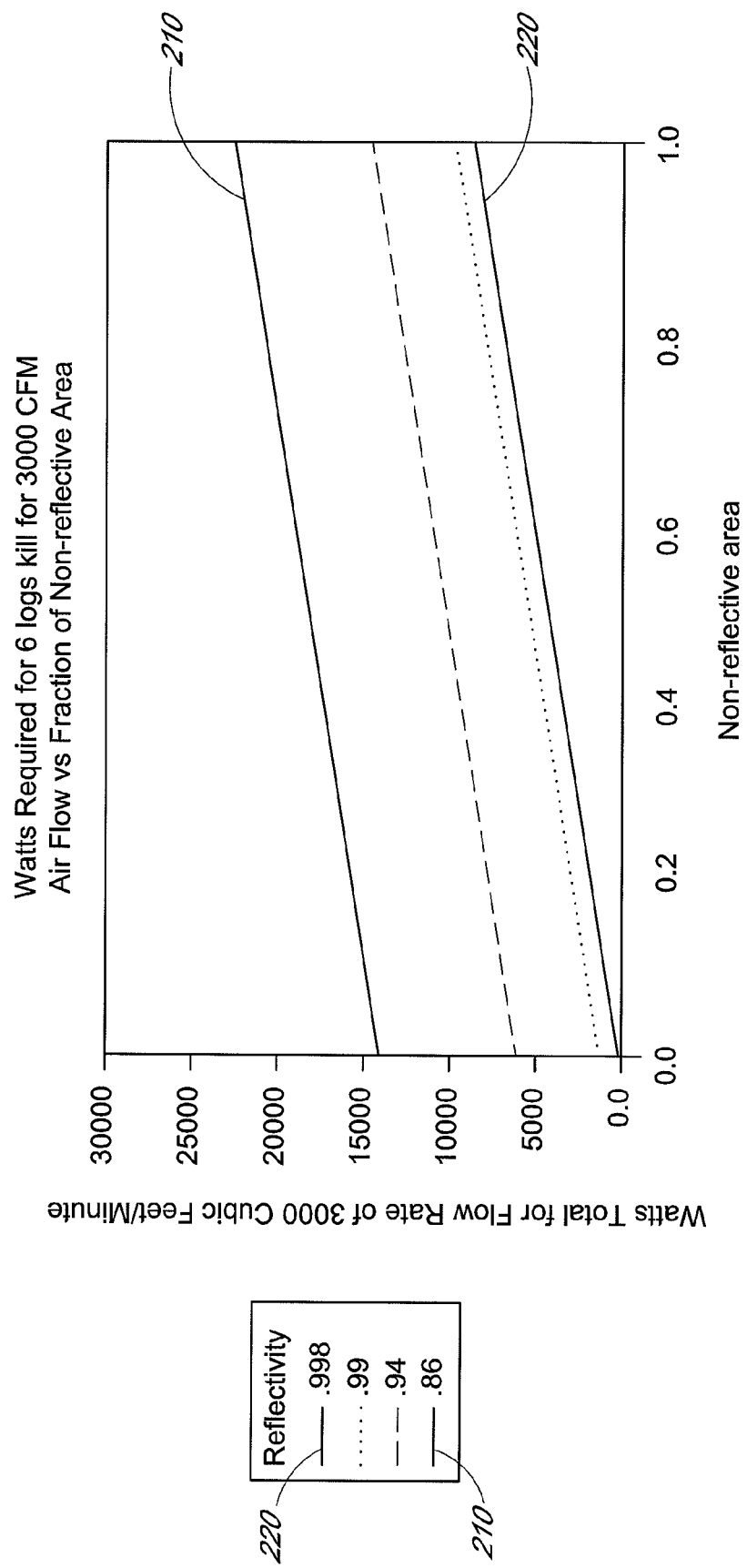
FIG. 2 is a graph illustrating the calculated power necessary to provide a specific microorganism kill rate.

Therefore, f=11.91/(10)=1.19 hertz, indicating that at the current velocity, the pulsed light source must flash 1.19 times per second. Finally, using $E_{total}$ and f found above, the approximate average power required may be estimated according to Equation 4. Specifically, $P_{average}=E_{total}*f$, thus $P_{average}$=430*1.19=512 watts FIG. 2 is a graph illustrating calculated power necessary to provide a specific microorganism kill rate in a sterilization chamber as a function of the percentage of the sterilization chamber surface area that is not highly reflective. This area is referred to herein as the "non-reflective area," and includes both "open area" and "absorbing area." Typically, the UV emitter (or emitters) within the sterilization chamber comprise the most significant source of absorbing area within the sterilization chamber. In one embodiment, the absorbing area of the lamp includes not only the outer surface area of the glass in the lamp, but also any wires, end connections, caps, and other components of the lamp disposed in the sterilization chamber. In an advantageous embodiment, the light absorbing surface area of the lamp is as small as possible, in order to reduce the non-reflective area of the sterilization chamber. The open area component of the non-reflective area typically comprises the open areas that allow light to exit from the sterilization chamber at the air inlet and outlet. As the amount of non-reflective area within the sterilization chamber decreases, the fluence of the light within the chamber increases, and the power necessary to provide a specific kill rate decreases.

FIG. 2 illustrates the power required for 6 logs kill in a sterilization chamber with air flowing at 3,000 cfm. The data represented in FIG. 2 was derived through tests using a sterilization chamber having dimensions of 120"×10"×10". The horizontal axis of FIG. 2 represents the fraction of non-reflective area in the sterilization chamber (including open area and absorbing area) and the vertical axis represents the power required to achieve the 6 logs kill in the sterilization chamber. There are four different data sets indicative of sterilization chambers having surfaces coated with materials having different reflectivities. For example, the lower solid line 220 is representative of a sterilization chamber having surfaces with a reflectivity of about 99.8% and the upper solid line 210 is representative of a sterilization chamber having surfaces with a reflectivity of about 86%. As the reflectivity of the surfaces in the sterilization chamber increases, the power necessary to achieve a certain kill rate decreases.

Furthermore, the chart of FIG. 2 indicates that as the percentage of non-reflective area decreases, the power required to achieve the desired kill rate decreases. Thus, in an embodiment having a reflectivity of 99.8%, as the non-reflective area approaches zero the required power is reduced to levels in the 200 to 700 watts range.

The characteristics of the light sources used in the sterilization chamber can have an important effect on the average power requirements. As can be seen from the above equations, the photon absorbing cross section of the light source directly influences the efficiency of photon multiplication in the chamber, making it advantageous to have light sources which absorb a minimum amount of light. Furthermore, reducing the number of emitters within a chamber may decrease the amount of light absorbed by emitters and, thus, decrease the total energy required to achieve a specific kill rate.

Another technique used to increase a kill rate of a sterilization chamber is to re-use light emitted from a light source. However, the openings for flow typically reduce effectiveness by allowing light to escape from the irradiation chamber. Thus, one aspect of the invention is to provide an air sterilization chamber that reduces the amount of light that escapes from the chamber and increases the amount of photons available in the chamber, while minimizing the pressure drop created.

It has been found that the use of packed arrays of fibers, spheres, or other small particles can provide many light scattering events such that the light incident on the packed array reflect back with high reflectivity, while the openness of the particle containment structure allows air flow with low pressure drop.

Figure 3A:
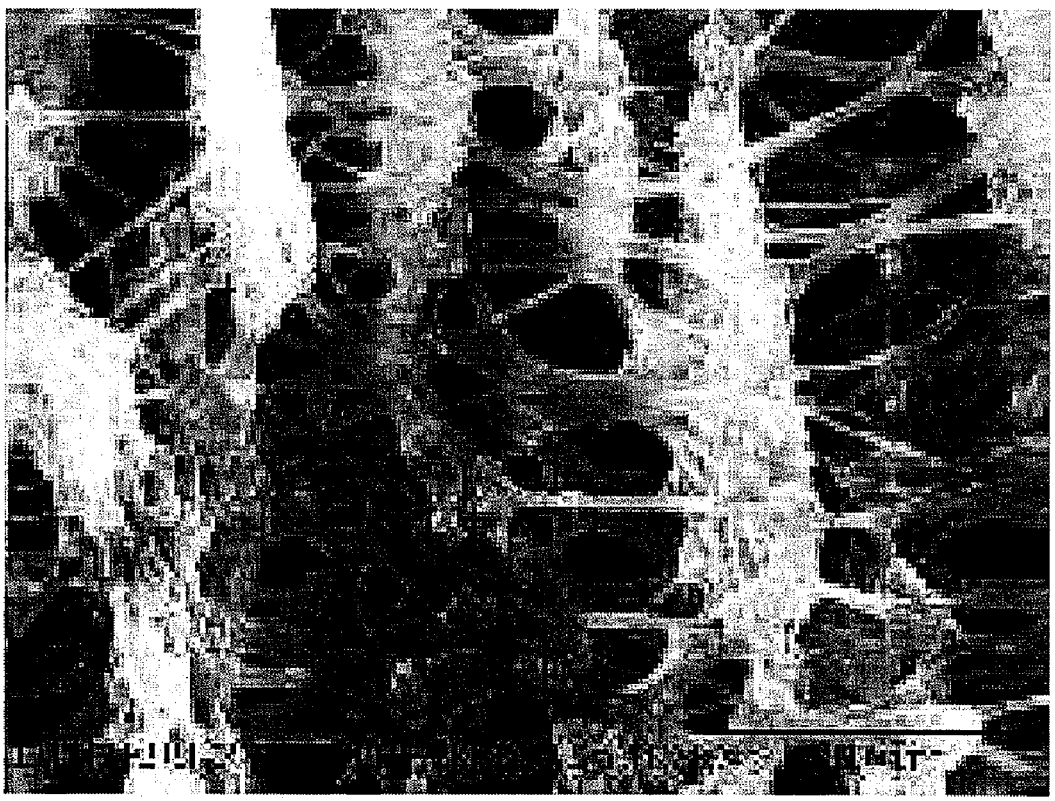
FIG. 3A is a photograph illustrating the structure of ePTFE.

DRP, an ePTFE (expanded PTFE) has a reflectivity of 99% or better in the UV. When PTFE (also known as Teflon®) is expanded, millions of microscopic pores are created in a three-dimensional membrane structure. These pores are smaller than almost any type of airborne or waterborne particulate, yet large enough to allow for the passage of gas molecules. In filtration applications, this allows air to pass through the membrane while collecting very tiny particulates on the slick membrane surface. ePTFE, which is produced with a pore structure, provides a structure that incurs minimal pressure drop while having light reflecting properties similar to DRP. FIG. 3A is a photograph illustrating the structure of ePTFE.

DRP, which is composed of ePTFE (expanded polytetrafluoroethylene) has a high reflectivity in the UV, approaching 100% (See U.S. Pat. No. 5,596,450, which is hereby incorporated by reference for all purposes). DRP is an example of a surface with high reflectivity based on favorable multiple scattering of light from the structure of the solid. Spectralon (See U.S. Pat. No. 5,462,705,) is another example of a highly reflective surface resulting from compaction of small fluorinated polymer components. for a patent describing this type of reflector is Seiner's U.S. Pat. No. 4,035,085, which is hereby incorporated by reference for all purposes. This Seiner patent describes methods of producing highly reflective coatings with fluorinated polymers and references the Kubelka-Munk scattering analysis.

Kubelka-Munk scattering describes reflectivity of paint and other surfaces and is based on the following assumptions:
1. particle size is <<layer thickness
2. isotropic scattering
3. particles randomly distributed
4. only diffuse reflection The theory describes the reflectivity, R as:

$$R = 1 - \sqrt{\frac{2K}{S}}$$

where: K=absorption coefficient=the limiting fraction of absorption of light energy per unit thickness, as thickness becomes very small.

S=the Scattering Coefficient=the limiting fraction of light scattered backwards per unit thickness as the thickness becomes very small.

A review paper by Pasikatan et al, J. Near Infrared Spectrosc. 9, 153-164 (2001), which is hereby incorporated by reference for all purposes, describes the Kubelka-Munk theory and derives expressions for K and S based on particle size, packing fraction etc.

The Pasikatan paper finds that the absorption coefficient in transmission is:

$$K_T = \frac{-3\Phi(D_M)\ln\left[1 - \frac{D(1-T_d)}{\Phi(D_M)}\right]}{2d}$$

where: d=particle diameter
D=packing density of particles
$D_M$=maximum packing density
$\Phi(D_M)$=a function of the maximum packing density
$T_d$=Transmittance of a single particle
$K_R$ for Reflectance is proportional to $K_T$ $$S \propto \frac{1}{d} \propto \frac{1}{\ell}$$

where l is the mean free path length between particles.

As d increases, $K_R$ and S decrease and radiation penetrates deeper into the material. This increases the path length that the light travels, thus increasing absorbance while reducing diffuse reflectance. As d decreases, light encounters more scattering boundaries (S increases) and the depth of penetration decreases. This decreases the path length l that the light travels, thus reducing the absorbed fraction of radiation and increasing the diffusely reflected fraction. This principle can be used to construct useful inlets and outlets to air sterilization chambers.

In one embodiment, a porous flux multiplying light trap may be used as an inlet or outlet of a sterilization chamber. In one embodiment, the porous flux multiplying trap comprises long fibers that each have low light absorption and high light scattering coefficients. The fibers may be arranged in a nonwoven fabric. The resultant apparatus can reflect light efficiently while allowing air to flow with low pressure drop. In an advantageous embodiment, the flow rate of air through the light trap is consistent across the whole surface of the apparatus, rather than having regions of high air flow and regions of low air flow. In one embodiment, the air flow rate through different regions of the apparatus varies by less than 50%. In another embodiment, the air flow rate through different regions of the apparatus varies by less than 30%, and more preferably by less than 20%. In addition, because the fibers have a high reflectivity and/or are coated with a material having high reflectivity, the fibers provide high reflectivity of light back into the sterilization chamber. Finally, a light trap having fibers will filter clumped biological material, removing the difficulties that can arise with killing this type of biological material with UV radiation.

Figure 3B:
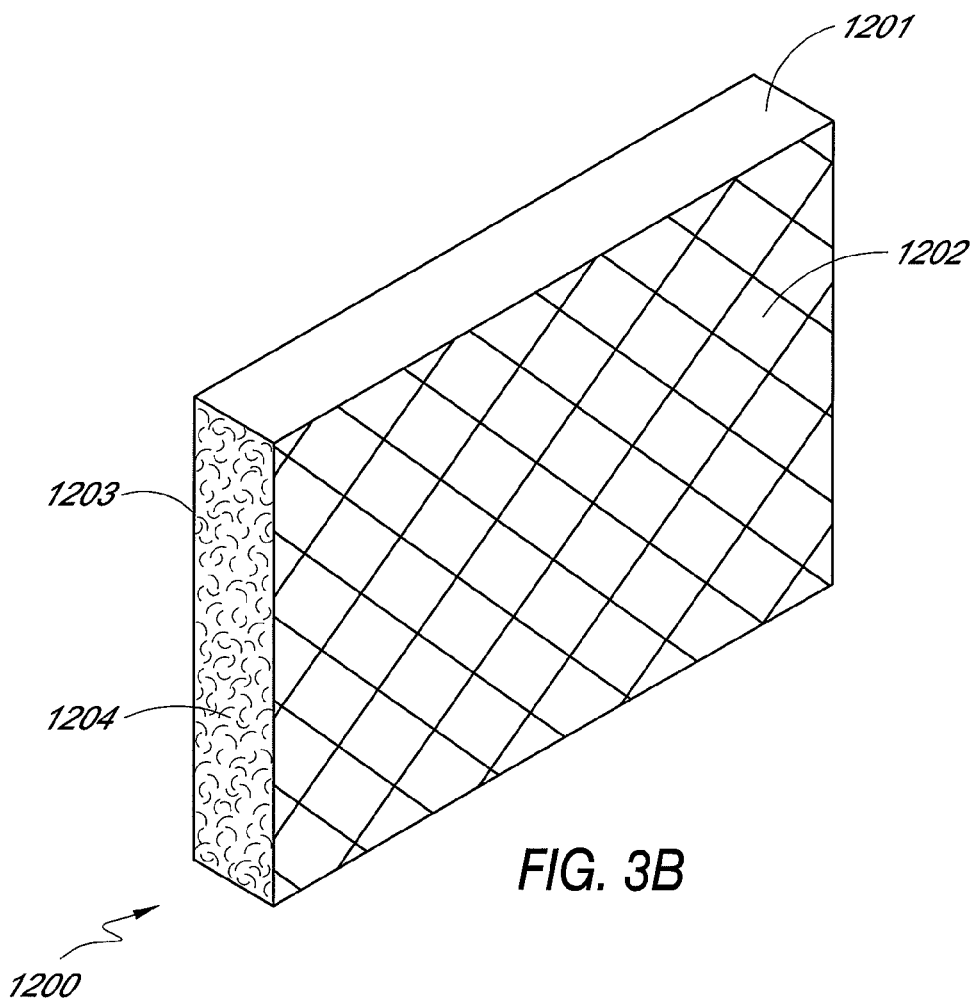
FIG. 3B is a perspective view of an aperture comprising fiber with high UV reflectivity that may be positioned at an inlet or outlet of a sterilization chamber.
Figure 3C:
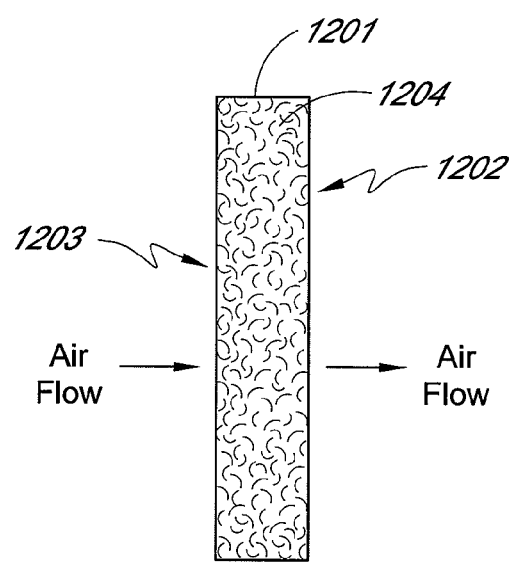
FIG. 3C is a cross sectional view of the aperture of FIG. 3B.
Figure 4:
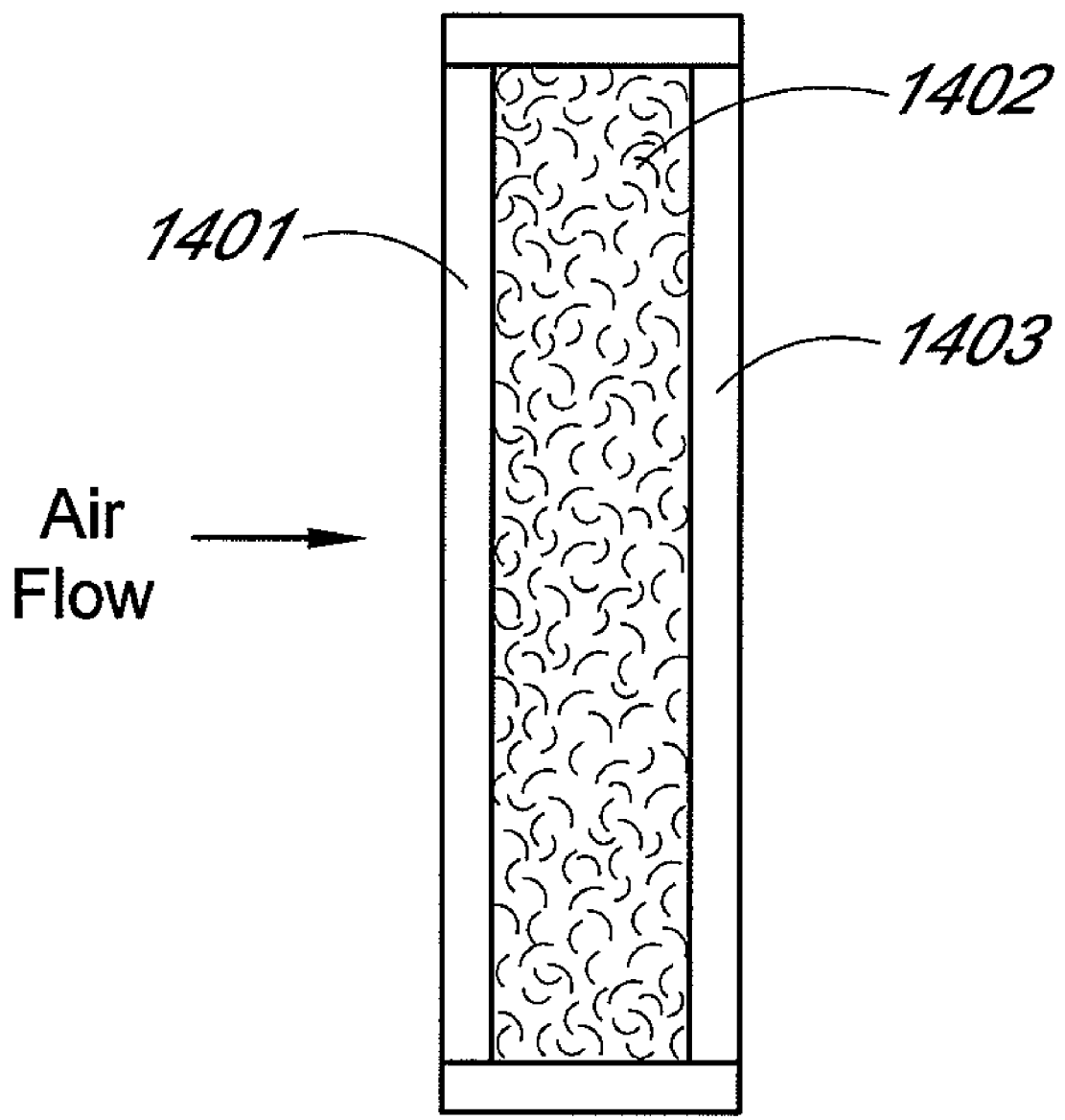
FIG. 4 is a cross sectional view of an aperture comprising small fibers with high UV reflectivity.

One embodiment of a porous flux multiplying light trap is shown in FIGS. 3B and 3C. The overall end or exit enclosure 1200 has a frame 1201 with containing structure 1202 and 1203 that enclose a mat of fibers 1204. These fibers can be composed of materials that diffusely reflect light and have low absorption of light. Example fibers include quartz and shredded polymers containing fluorine, such as PTFE. In one embodiment, the frame 1201 comprises a filter material of ePTFE with pore sizes about 3 times greater than the material in the frame. Additionally, imbedding of various oxides or other additives may be performed to further enhance reflectivity. Other materials that can be used are plastics such as polystyrene, Teflon, latex, rubbers, and natural fibers such as cotton. In one embodiment, the inside facing surfaces of the material in the frame 1201 are impregnated with UV reflecting compounds to further increase the reflectivity of the light within the sterilization chamber. For example, chemical destruction in the flowing air could also be facilitated by impregnating the ePTFE with photocatalyst material such as $TiO_2$.

In another embodiment, the inlet and outlet of a flux multiplying light trap comprises small particles that satisfy the K-M theory well and are also packed in a manner to meet the requirements of the scattering theory (e.g., packing fraction.) The small particles can be crystals of materials such as $Al_2O_3$ or $TiO_2$. They can also be larger particulates up to 50 or 60 microns in diameter. One possible structure is shown in cross section in FIG. 4. Grids 1401 and 1403 provide mechanical support to the scattering material 1402 that is held in the frame 304. The grids 1401 and 1403 may be metal or plastic screen, for example, with a large open area, such as a window screen. It may also be a screen made of woven quartz fibers or threads.

EXAMPLE 2

A complete reflecting end with dimensions 20"×40" and approximately 2" thick was constructed using 1 pound of quartz wool. A mesh (chicken wire, readily available from hardware supply stores) was used to contain wool fibers. An entrance plate to the chamber was removed. The exit plate was unchanged and a calorimeter placed on the entrance.

Experiment 2.1

No reflecting components were placed at the entrance opening, so the open area at the entrance was 100%. The flux was 32 mW/cm$^2$ with a single lamp on.

Experiment 2.2

A continuous sheet of DRP reflective material 20"×28" was placed over the entrance. The open area is therefore 30% of the total entrance area. The flux was 71 mW/cm$^2$.

Experiment 2.3

The previously described porous reflector was placed at the entrance in place of the 20"×28" sheet of DRP. The resulting flux was 72 mW/cm$^2$.

These experiments 2.1 through 2.3 show that the porous reflector has the same effect on flux inside the test duct as a single sheet of highly reflective material that covers only 70% of the entrance into the test duct. Therefore the average reflectivity of the porous reflector was about 70%.

All these experiments were conducted with readily available materials. No effort was made to optimize the reflecting material properties that are relevant from the K-M theory (e.g., packing fraction or particle reflectivity), and an absorbing metal mesh was used to provide mechanical support to the assembly. It is expected that the reflectivity will approach 100% with appropriate choice of particle or fiber sizes and reflecting properties.

In yet another embodiment, the porous inlet and outlet of a flux multiplying light trap comprises pellets or powders or shavings of materials that have low absorption and high scattering coefficients. The materials may be, for example, specially prepared PTFE, a mixture of a binder and reflecting additives such as barium sulfate, magnesium fluoride, magnesium oxide or aluminum oxide, holmium oxide, calcium oxide, lanthanum oxide, germanium oxide, tellurium oxide, europium oxide, erbium oxide, neodymium oxide, samarium oxide or ytterbium oxide, quartz, sapphire, PTFE, barium oxide, shredded ePTFE or polyethylene. Alternatively, pellets, powders or shavings of material that are coated with suitable coatings may also be used. One such material is quartz beads covered with a highly reflective coating of PTFE or aluminum. The pellets, powders or shavings are held inside the assembly by a retaining structure on each side suitable for retaining the pellets, powder or shavings while allowing air to pass through with low pressure drop. One such retaining material is common window screening, which is typically made of plastic, aluminum or copper. Another material is loosely woven quartz fabric, which minimizes absorptions at the retaining structure.

In still another embodiment, the non-woven reflecting material may be strengthened by weaving strengthening members into the non-woven reflector. This may be done with rigid strengthening members such as quartz or aluminum rods or by quilting the non-woven reflector, or by weaving or sewing strengthening fibers such as Kevlar or carbon into the non-woven reflector. Such an embodiment would reduce the absorption of the strengthening mesh previously described and so increase the overall reflectivity of the porous reflector.

A further embodiment provides structural support to the non-woven reflecting material via pleats in the material and supporting rods or wires at the bends in the pleats. Additionally, the non-woven material may be structurally supported by bonding the material from front to back with a thin line of bonding agent such as epoxy or silicone. The rigidity of the bond provides sufficient strength to the non-woven material that it can withstand the force of the air flow without bending.

For sterilization applications, the porous reflector should reflect UV wavelengths with little loss. More specifically, it should reflect light in the germicidally active wavelengths with low loss. This wavelength band is generally though to be from 200 to 300 nm.

In summary a flux multiplying light trap with no moving parts comprises an apparatus that traps light with highly reflective walls and highly reflective and porous end pieces that allow low pressure drop in flowing air while reflecting a significant fraction of light has been described. Furthermore, the use of highly reflective fibers in configuration other than in the above-described filter configuration may provide substantially similar results.

In the above-described embodiments, the configuration of the sterilization chambers is such that the lamps are located in the sterilization chamber, and, as a consequence, are in the flow of the air through the sterilization chamber. In one embodiment, nonuniformity caused by placing the lamp in the sterilization chamber is reduced by placing the lamp outside of the direct path of air flow within the chamber. In this way, a more uniform illumination in an HVAC duct may be achieved while maintaining a uniform flow distribution. For example, they can be applied to water treatment, to UV curing, and to killing organisms on three dimensional objects.

In one embodiment, a lamp (for example, a pulsed, microwave excited, medium pressure mercury arcs or germicidal lamp) is located in a separate lamp holder chamber and transmits the light into the HVAC duct or sterilization chamber through a window. The window may be a quartz plate or it may be open. By placing the lamp outside of the direct path of air flow, several advantages may be realized. In particular, the flow of air is not disturbed by the lamps. Similarly, the lamps are not contaminated by the flow of air when a window, such as a quartz window, separates the lamps from the sterilization chamber. Also, because the lamp is outside of the sterilization chamber (or HVAC system), high flow rates in small duct sections may be more adequately sterilized by using a UV lamp that may be too large to fit inside the duct. Furthermore, the lamps can be replaced without turning off the HVAC system. Also, the lamp operating temperature can be independent of the HVAC air flow temperature, improving lamp performance. Finally, heat generated by the lamps is not deposited in the HVAC duct air flow. These and other advantages will be discussed in further detail below with reference to certain exemplary embodiments.

Figure 5A:
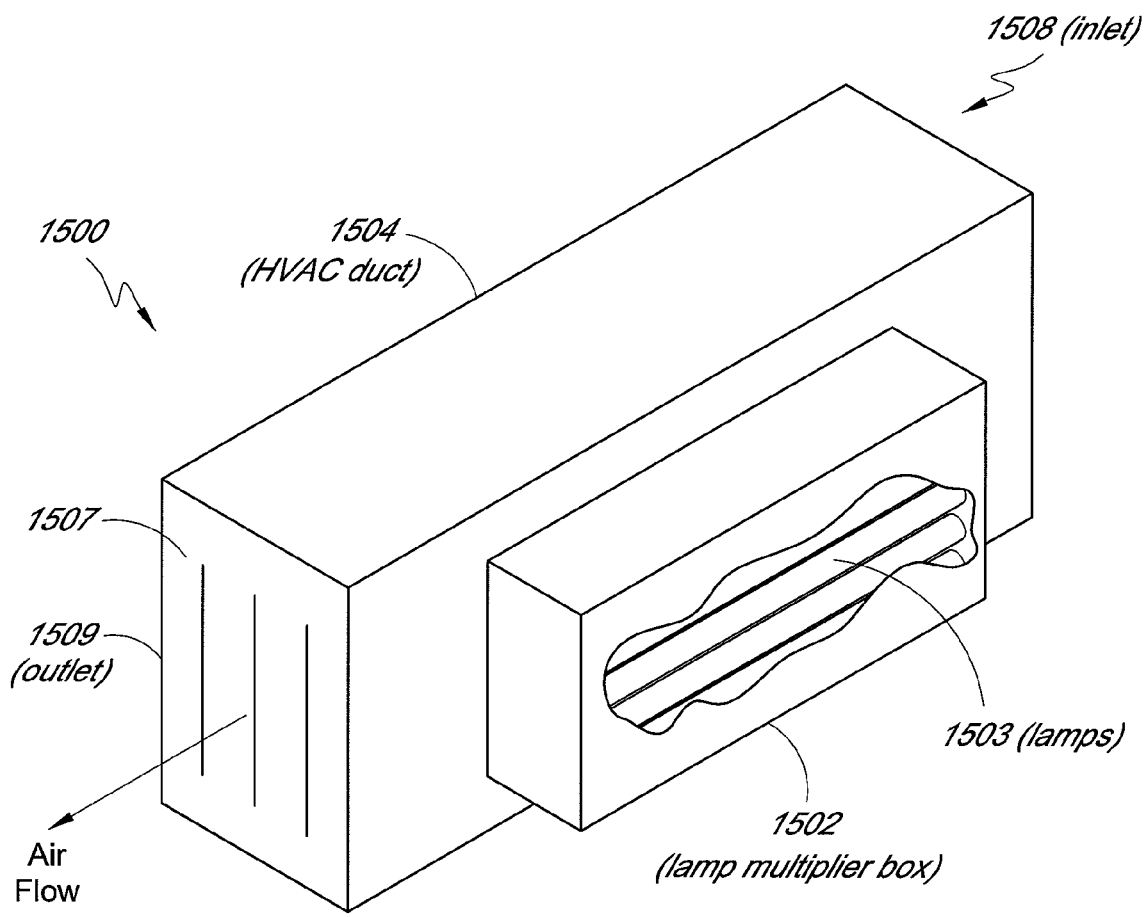
FIG. 5A is a schematic of a lamp multiplier box attached to a HVAC duct.

FIG. 5A is a perspective view of an exemplary sterilization chamber 1500 including a HVAC duct 1504 that includes at least one inner surface lined with a diffuse reflective material. The sterilization chamber 1500 is equipped with light enhancement reflectors 1507, such as the photon trap described above, at the inlet 1508 and the outlet 1509. A Light Multiplier Box 1502 is attached to the HVAC duct 1504.

Figure 5B:
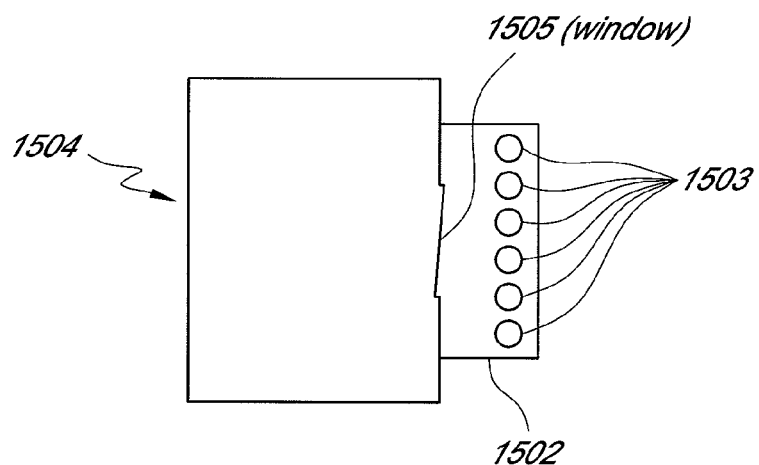
FIG. 5B is a cross sectional schematic of a lamp multiplier box attached to a HVAC duct.

FIG. 5B is a cross-sectional side view of the HVAC duct 1504 in FIG. 5A, where the cross-section is across the lamp box multiplier 1502. As illustrated in the exemplary embodiment of FIG. 5B, between the lamp box multiplier 1502 and the HVAC duct 1504 is a connecting window 1505 for transmission of light into the HVAC duct 1504. The light multiplier box 1502 includes one or more sterilization lamps 1503. In one embodiment, the window 1505 is a UV transparent material such as quartz or UV transparent plastic. In one embodiment, the walls of both the HVAC duct 1504 and the lamp multiplier box 1502 are lined with material that has a high reflectivity, advantageously greater than 86% and may be either Lambertian or specular. Examples of appropriate material are DRP, Spectralon or Alzak. The window 1505 is preferably sufficiently large to allow the maximum transfer of energy between the light multiplier box 1502 and the HVAC duct 1504. An approximation of the UV flux available in the HVAC duct 1504 can be obtained under the large window assumption by treating the system mathematically as one box.

EXAMPLE 3

Single Germicidal Lamp in Lamp Multiplier Box

| HVAC Duct Dimensions. | |
| --- | --- |
| Boxlength | 80 inches |
| Boxwidth | 20 inches |
| Boxheight | 40 inches |
| Percent Open Ends | 14% |
| Lamp Multiplier Box Dimensions | |
| Boxlength | 40 inches |
| Boxwidth | 3 inches |
| Boxheight | 40 inches |
| Window Dimensions | |
| 40 inches × 40 inches | |
| Lamp length | 40 inches |
| Lamp Diameter | 1.3 inches |
| Reflectivity | 0.99 |
| Absorption of lamps per pass | 4% |
| UV output | 64 watts, CW |

For a flow rate of about 3500 cubic feet per minute, this would result in a kill of *Bacillus subtilis* to about 1.15 logs. The power to the lamp would be about 340 watts.

EXAMPLE 4

Multiple Germicidal Lamps in Lamp Multiplier Box

As illustrated in the exemplary embodiment of FIG. 5B, the lamp multiplier box 1502 houses multiple germicidal lamps 1503. Because the multiple germicidal lamps 1503 are placed outside of the duct 1504, their presence does not disturb the flow of air or the uniformity of exposure. In the embodiment of FIG. 5B, six lamps are placed in the lamp multiplier box 1502. At a flow rate of about 3500 cubic feet per minute, this would result in a kill of *Bacillus subtilus* to about 6.1 logs. The power to the lamp would be about 2390 watts.

Prior art sterilization systems, for example the system described in "Defining the Effectiveness of UV lamps Installed in Circulating Air Ductwork," RTI International, November 2002, illustrates an irradiance distribution in a galvanized duct with a peak irradiance of 0.0016 watts/$cm^2$. At this fluence, the duct would need to be 0.4 miles long to kill to this level at 3500 cfm. This is because the duct is arranged so that power is not combined within the duct.

With the above-described embodiments, germicidal lamps, which normally treat at a low flux and require large systems, can provide much higher doses and effectively kill organisms at high flow rates. This unexpected advantage of our concept allows these efficient, inexpensive germicidal lamps to perform functions which have previously been the domain of higher power medium pressure arcs or flash lamps.

FIG. 6 is a perspective view of another embodiment of an air sterilization chamber 900. The sterilization chamber illustrated in FIG. 6 comprises another embodiment having inlet and outlet areas that are highly reflective and require no moving parts. In the specific embodiment of FIG. 6, the sterilization chamber 900 is geometrically shaped as a parallelepiped. A parallelepiped shaped sterilization chamber may provide a geometry that is advantageous for modularly combining multiple sterilization chambers 900. The chamber could also be circular or elliptical in cross section.

The sterilization chamber 900 of FIG. 6 comprises a front panel 910 connected to end panels 920 and 930. The front panel 910 is parallel to a rear panel 960, both of which are connected to a bottom panel 950 and a top panel, which is not shown in FIG. 6, but in practice would be used. Further, in the illustration of FIG. 6, the front panel 910 is partially cut-away in order to illustrate components internal to the sterilization chamber 900. In one embodiment, one of the panels is easily removable from the sterilization chamber 900, thus allowing easy access to the inside of the sterilization chamber 900 for cleaning or maintenance of the components therein.

As noted above, the end panels of the sterilization chamber illustrated in FIG. 6 comprise no moving parts. In addition, the end panels are advantageously highly reflective and are arranged so that the amount of light that exits from the chamber is minimized. End panels 920 and 930 comprise an entrance and exit, respectively, for air flow. As shown in FIG. 6, end panel 920 comprises two rows of offset slats 922 and 924. The slats are offset so that air may pass through the end panel 920. In an advantageous embodiment, the sterilization chamber 900 is substantially air tight except for the entrance and exit created by end panels 920 and 930. In other words, air may only enter and exit the sterilization chamber 900 through end panels 920 and 930. Additionally, the inner surfaces of the offset slats 922 and 924 comprise a highly reflective material so that light is substantially contained inside the sterilization chamber 900. In short, the end panels 920 and 930 are constructed so as to allow air flow in to and out of the chamber while decreasing the amount of light that exits the air treatment chamber 900. Other configurations of end panels that route air through the sterilization chamber while blocking light from exiting the chamber may accomplish similar results. For example, an end panel may comprise two sheets of highly reflective material each having a plurality of holes in different positions, such that when the sheets are mounted in parallel as an end panel to a sterilization chamber, there are no overlapping holes. The sheets may be mounted parallel to one another so that there is a gap large enough to allow air to flow between the sheets, thus allowing air to pass through the end panel, while blocking light from exiting the end panel. In addition, as will be illustrated in FIGS. 12-15, a plurality of different mechanisms (such as the moveable flaps in FIG. 12, sliding flaps in FIG. 13, and the rotating drums in FIG. 15) may be used in order to reduce the open area of the sterilization chamber, and, thus, increase the flux density inside the chamber.

An UV emitter 320 is operatively coupled between the front panel 910 and the rear panel 960 so as to emit UV light inside the sterilization chamber 900. In the embodiment of FIG. 6, the UV emitter 320 is mounted substantially in the center of the rear panel 960 and parallel to the bottom panel 950 and end panel 920. However, it is contemplated that the UV emitter 320 may be mounted on any panel and oriented in any direction. Certain types of UV emitters may produce significant heat so that the emitter requires external cooling. Therefore, in one embodiment, the end panels 920 and 930 may be adapted to increase the air flow directly over the UV emitter 320 to provide cooling of the UV emitter 940. In addition, the UV emitter 320 may be placed in a different location so that more air flows over the UV emitter 320.

The UV emitter 320 emits light at a wavelength and intensity so as to kill microorganisms and break up or destroy harmful chemicals. Thus, depending on the types of microorganisms and chemicals which are primarily targeted, the UV emitter 320 in different sterilization chambers may emit light at different wavelengths and intensities. For example, in one embodiment, the UV emitter 320 may emit energy in the 170 to 400 nanometer wavelength range. In another embodiment, the UV emitter 320 may emit energy in the 200 to 300 nanometer wavelength range. In another embodiment, the UV emitter 940 may be replaced by an emitter that emits light at wavelengths outside the UV band. Likewise, in one embodiment, the UV emitter 320 may emit some light having UV wavelength and some light having wavelengths outside of the UV band. In another embodiment, the UV emitter 320 is interchangeable with other UV emitters having different operational characteristics, such as wavelength and intensity. In one advantageous embodiment, the sterilization chamber 900 may sterilize air at a rate of about 200 to 300 cubic feet per minute (cfm). In addition, multiple sterilization chambers 800 may be operatively coupled together in modular combination to sterilize air at a rate of more than 30,000 cfm. Of course, one of skill in the art will realize that the air flow rate may be adjusted by changing the number of modular sterilization chamber in a particular air duct.

As discussed above, in advantageous embodiments, the inner surfaces, e.g. the surfaces exposed to the UV emitter 320, of each of the panels 910, 920, 930, 950, 960, and the top panel (not shown) comprise a highly reflective material having a diffuse reflective behavior. As such, light rays incident on the diffuse reflecting surface (also referred to as a surface having a diffuse reflective behavior) are scattered over the hemisphere of the reflective surface, increasing the fluence within the sterilization chamber 900.

The air flow in a chamber, such as the sterilization chamber 900, is characterized by a velocity distribution which can be laminar, e.g. with a parabolic distribution vs velocity, or turbulent, e.g. with a flatter velocity profile. The kill rate within any particular sterilization chamber 900 is thus affected by the particles with the greatest velocity.

Slats in the inlet or outlet can accelerate the air flow, leading to an increased fraction of air molecules or entrained spores and chemicals moving at high velocities. These high velocity components pass through the chamber faster and thus receive a lower dose of UV. It is advantageous to have a means of slowing these accelerated particles down.

Figure 7:
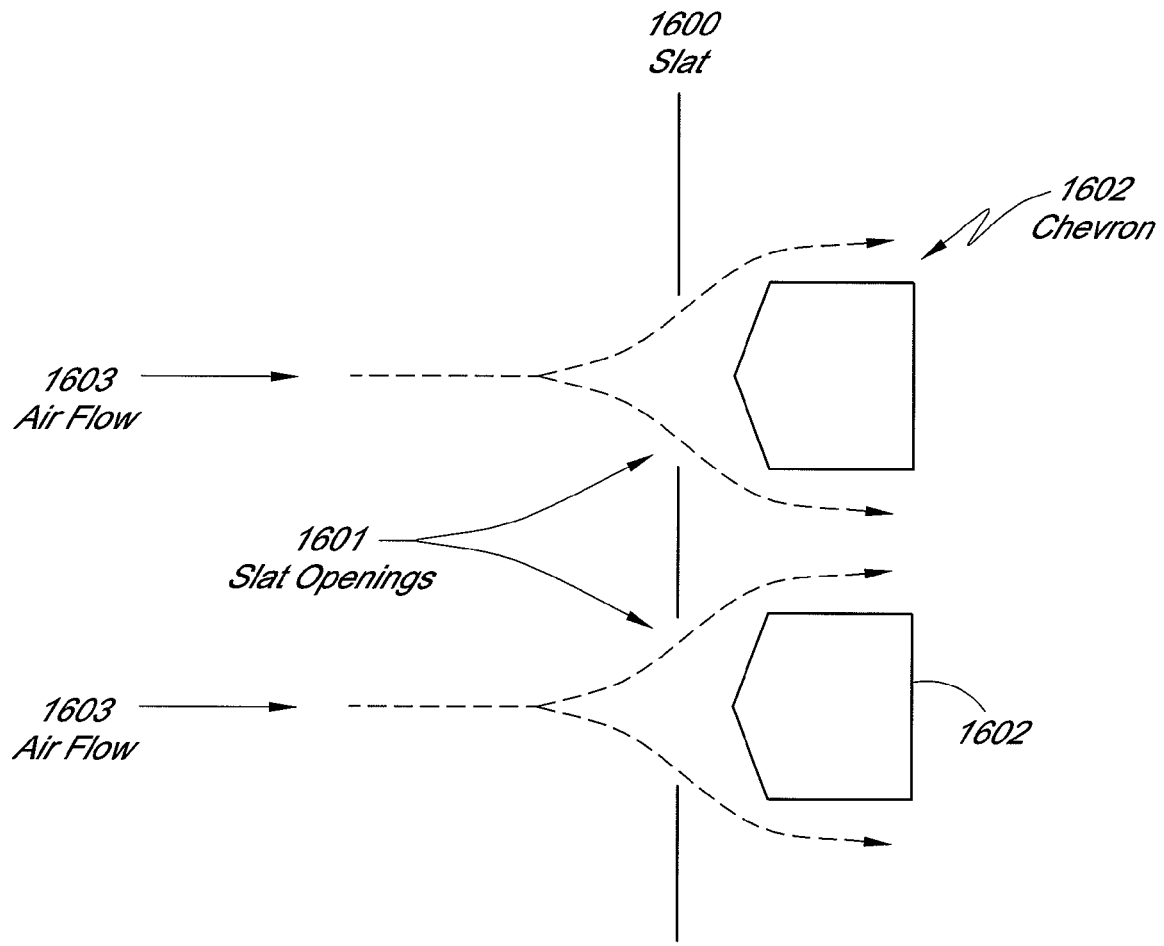
FIG. 7 is a diagram illustrating air flow around triangular wedges, or chevrons which may be placed at the inlet and/or outlet of a sterilization chamber or HVAC duct.

FIG. 7 is a diagram illustrating air flow around an air spreader. The air spreaders may be of any shape, and are advantageously triangular or chevron shaped. In the embodiment of FIG. 7, the air spreaders are shaped as chevrons 1602, which may be placed at the inlet and/or outlet of a sterilization chamber. The concept for slowing this "jetting" air is to place an aerodynamically shaped chevron 1602 at the outlet of each slot 1602 to spread out the flow and decrease the flow velocity. Thus, the slat 1600 has openings 1602 for air flow 1603. A chevron 1602 is placed directly in the front of each opening 1603 to force the air to expand and slow down.

Figure 8:
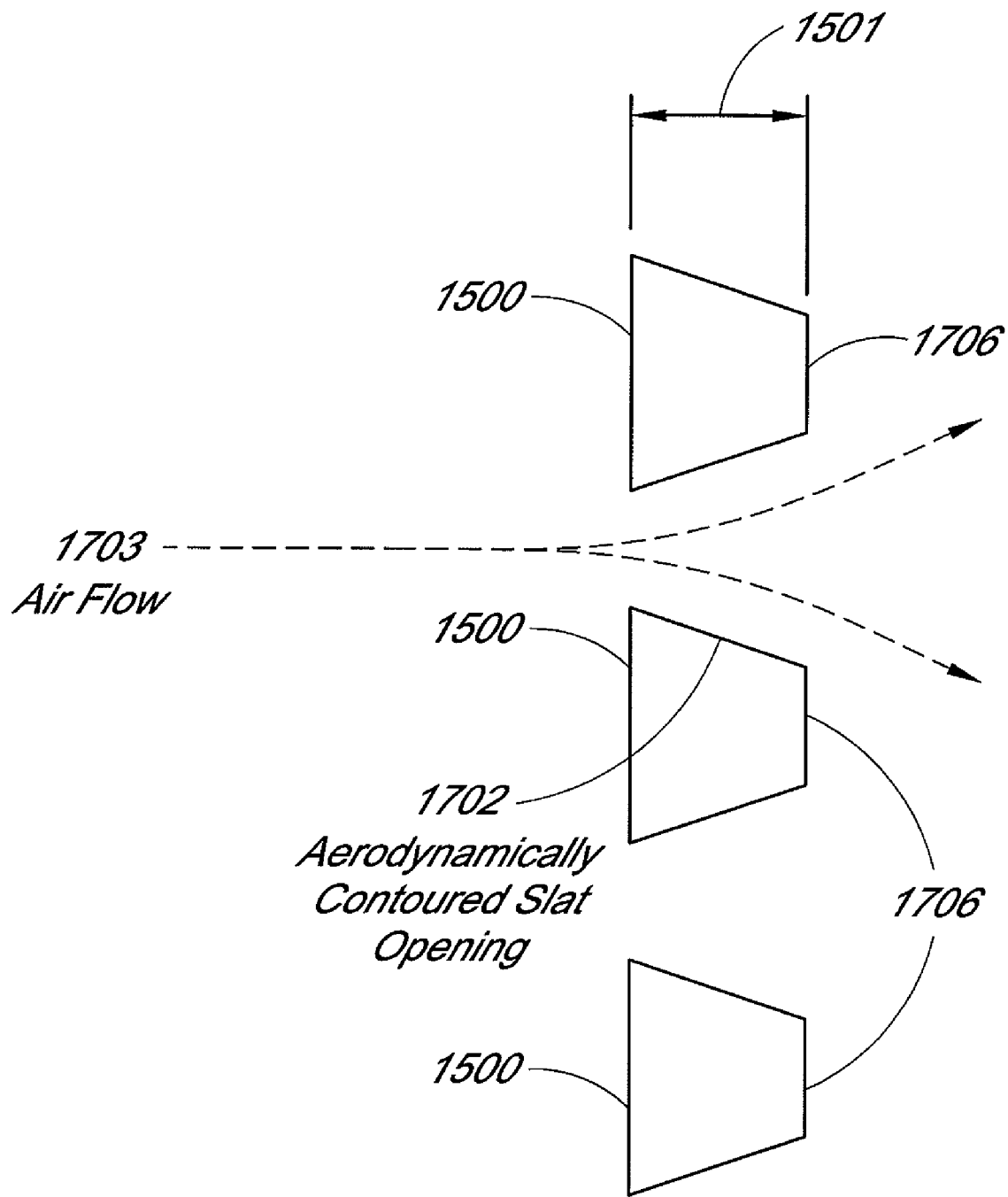
FIG. 8 is a diagram illustrating air flow around aerodynamic contours that may be placed at the inlet and/or outlet of a sterilization chamber or HVAC duct.

FIG. 8 is a diagram illustrating air flow around another embodiment of air spreaders. In the embodiment of FIG. 8, the air spreaders comprise aerodynamic contours 1706 that may be placed at the inlet and/or outlet of a sterilization chamber. The contours 1706 advantageously slow the "jetting" air. The slat 1700 comprises one or more aerodynamic contours 1706, each having a finite width 1701 so that the air flow 1703 expands as it goes through a gap between the aerodynamic contours 1706. In one embodiment, the aerodynamic contours 1706 are angled about 3.5 degrees to the flow direction to allow expansion of the air flow without separation from the walls.

The chevrons 1602 and aerodynamic contours 1706 are two structures that exemplify the concept of shaping the air. It is expressly contemplated that other structures that provide a reflecting surface and minimizes the spatial variations in air flow velocity, such as intricate air foils, for example, may achieve similar advantages as those discussed above.

Figure 9:
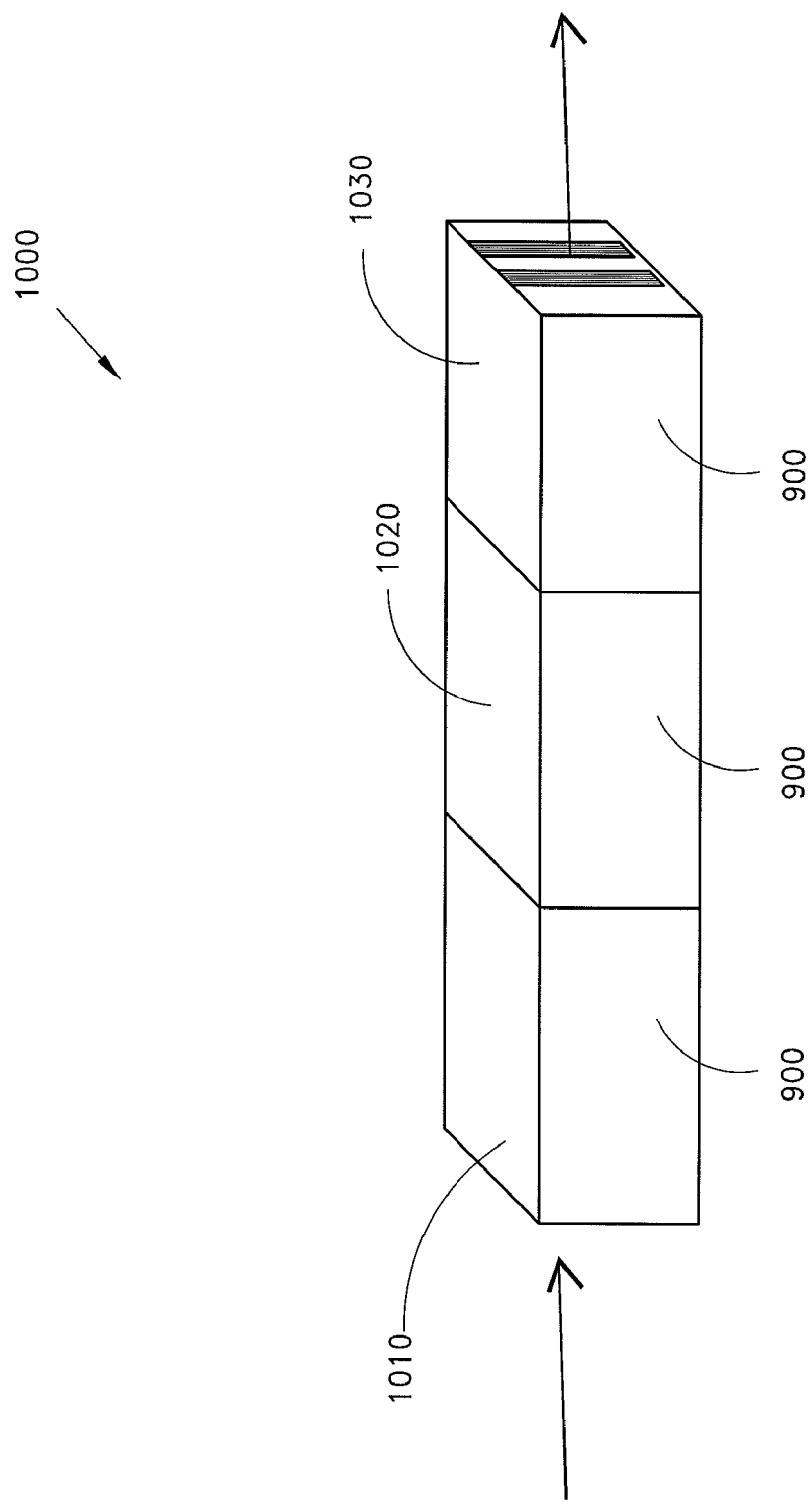
FIG. 9 is a perspective view of three modular sterilization chambers operatively coupled together in a series configuration.
Figure 10:
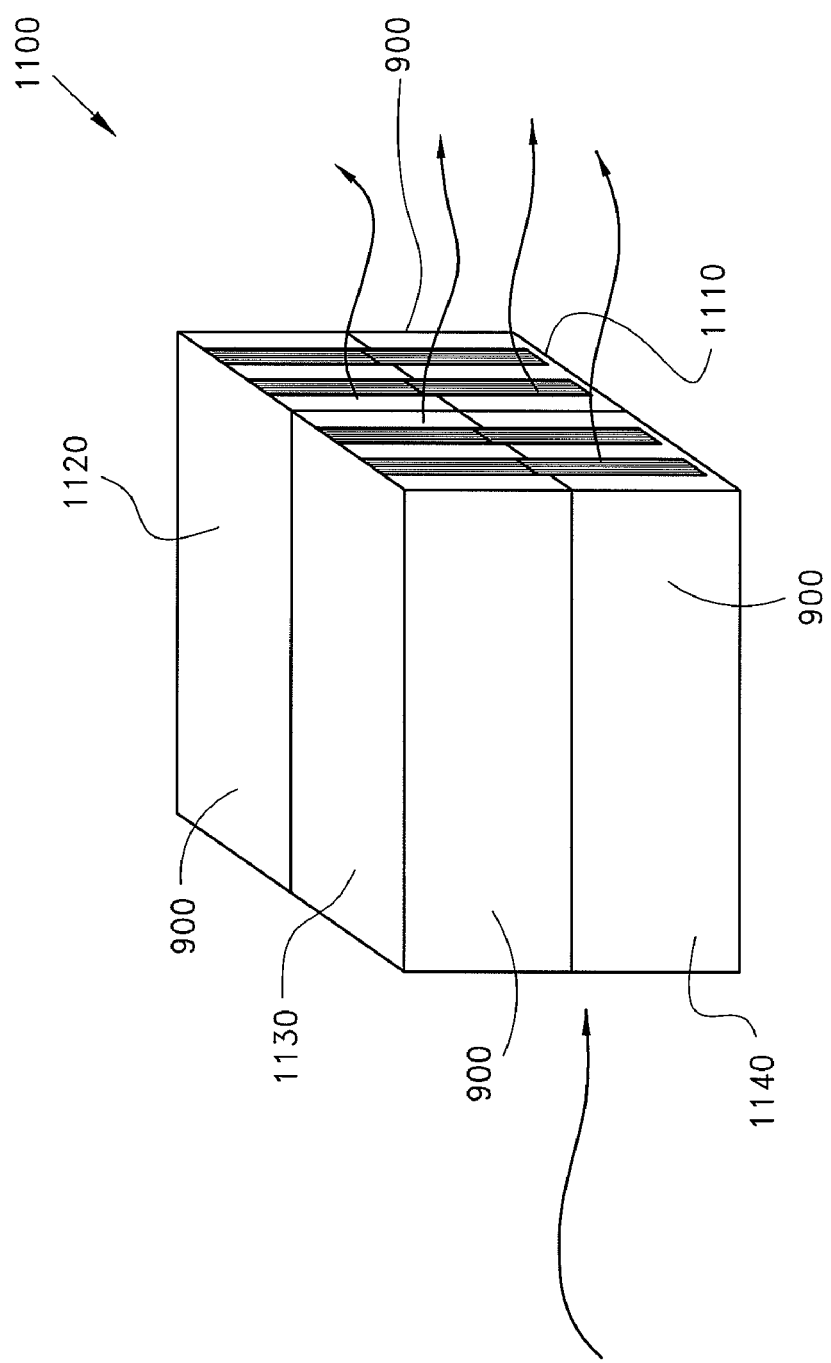
FIG. 10 is a perspective view of four modular sterilization chambers operatively coupled together in a parallel configuration.

Parrallelipiped chambers can be treated as modules and assembled in various fashions. FIG. 9 is a perspective view of three modular sterilization chambers, according to another embodiment, operatively coupled together in a series configuration while FIG. 10 is a perspective view of four modular sterilization chambers, according to another embodiment, operatively coupled together in a parallel configuration. In one advantageous embodiment, a combination of modular sterilization chambers, such as sterilization chamber 900, may sterilize air for an entire building. For example, if an individual sterilization chamber 900 sterilizes air at a rate of 300 cfm, a combination of 6 sterilization chambers 900 may sterilize air at a rate of about 1800 cfm. As indicated by the arrows on either end of the modular combination 1000, contaminated air enters the modular sterilization chamber 1010, passes through modular sterilization chamber 1020, and finally exits modular sterilization chamber 1030. In this case, each microorganism, or other contaminant, sequentially passes through three separate sterilization chambers. Conversely, in the embodiment of FIG. 10, air enters each of the sterilization chambers 1110, 1120, 1130, and 1140 of modular combination 1100 at substantially the same time. Therefore, in this parallel configuration, each contaminant passes through only one of the sterilization chambers.

Each of the modular sterilization chambers 1010, 1020, 1030, 1110, 1120, 1130, and 1140 may have geometries similar to that of the sterilization chamber 900, or, alternatively, may have other geometric structures. As a result of coupling together multiple sterilization chambers, the effective kill rate of the modular combinations 1000 and 1100 may be increased as the air passes through each successive chamber. The modular combinations 1000 and 1100 may provide a much higher kill rate when compared to a single sterilization chamber having about the same air flow rate. Likewise, in comparison to a single sterilization chamber, the modular combinations 1000 and 1100 may provide a similar kill rate with a flow rate through each chamber of about ¼ that of the single sterilization chamber.

Alternatively, the rate of air flow may be increased, compared to the air flow rate through a single sterilization chamber, while achieving a similar kill rate. For example, if the sterilization chamber 900 has a flow rate of 695 cfm, the combination of the three sterilization chamber 1010, 1020, and 1030 in series would provide a substantially identical kill rate at about three times the flow rate (about 2085 cfm) through the three chambers.

While the modular combination 1000 illustrates three sterilization chambers connected in series (end to end), and the modular combination 1100 illustrates four sterilization chambers connected in parallel (side by side), it is also anticipated that any number of sterilization chambers may be connected in any configuration. For example, in one embodiment, 2 sterilization chambers may be operatively coupled in parallel, such that the chambers are side by side or on top of one another. Likewise, in another embodiment, any number of sterilization chambers may be connected in series to satisfy particular flow rate and kill level requirements. In yet another embodiment, any number of sterilization chambers may be connected in both series and parallel to satisfy particular flow rate, kill level and space or layout requirements.

Figure 11:
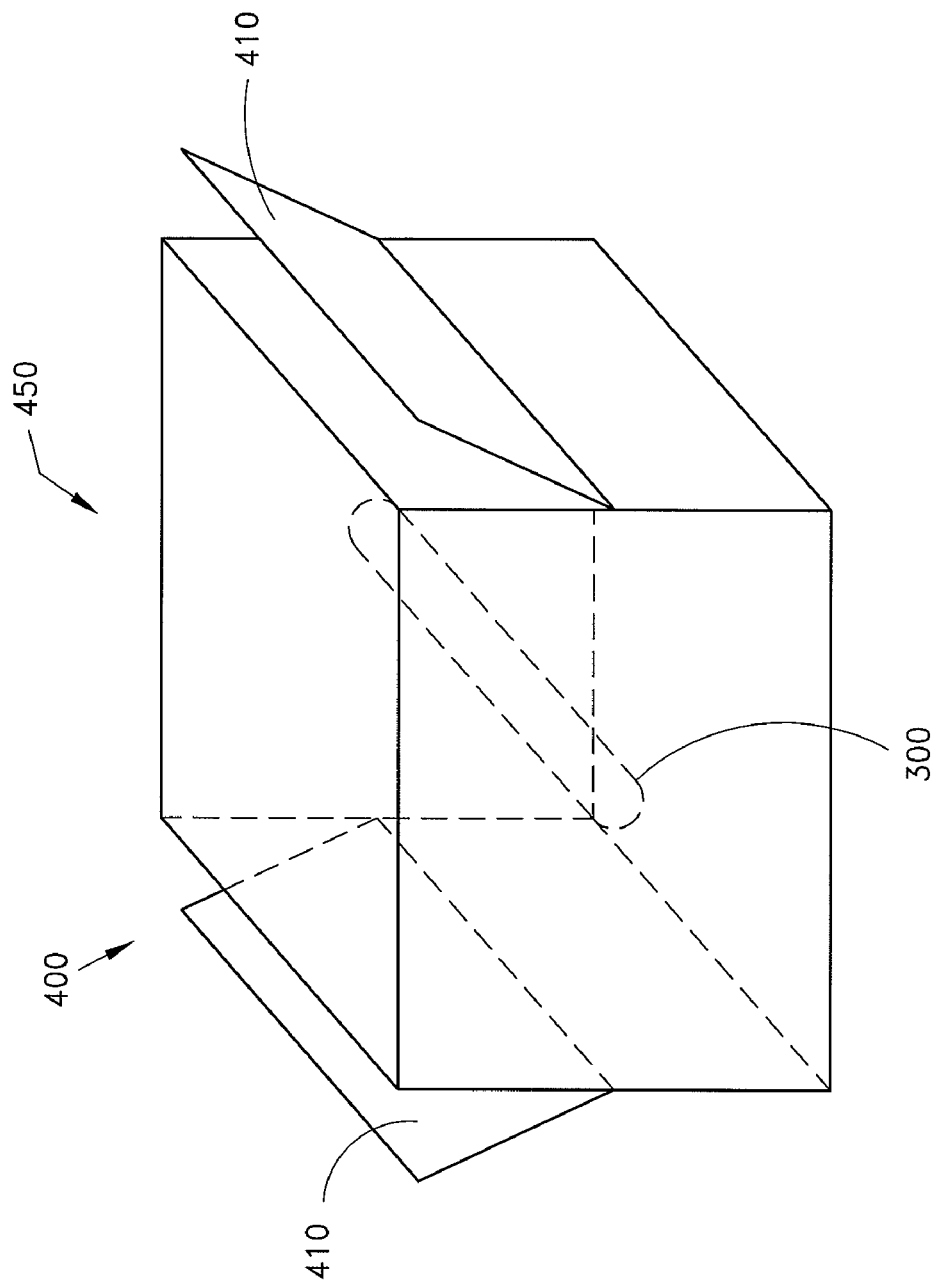
FIG. 11 is a perspective view of an embodiment of an air sterilization chamber with the end flaps open.

FIG. 11 is a perspective view of an embodiment of an air sterilization chamber 300 with an inlet aperture 330 and an outlet aperture 340 comprise moveable end flaps 310 that are configured to open and close in order to selectively block light emitted from the light source 320 from exiting the sterilization chamber 300. In one embodiment, the end flaps 310 are hinged to the ends of the sterilization chamber 300. As such, the flaps 310 can be rotated to close off the air inlet and the air outlet. In an advantageous embodiment, when in the closed position, the surfaces of the flaps 310 facing the emitter 320 comprise reflecting material with a high reflectivity so that the total energy required to achieve a specific kill rate ($E_{total}$) may be further decreased. More specifically, as the open area of the sterilization chamber approaches zero, the ratio of non-reflective area to inner surface area (where the ratio is referred to as α) is decreased and, thus, the value of $E_{total}$ is also decreased. With the inner surface of the sterilization chamber 300 substantially lined with 99.8% reflective material, the power required for killing to six logs with 10,000 cfm drops to around 900 watts, which is typical of many small appliances.

In an advantageous embodiment, the end flaps 310 are opened and closed in sync with the flashing of the emitter 320. In particular, the end flaps 310 may be timed to close before the emitter flashes and open after the emitter flashes. Thus, the opening and closing of the flaps 310 is synchronized around the pulsing of the emitter so that the open area is decreased when light is emitted from light source 320 while maintaining sufficient air through the sterilization chamber 300 between pulses of light from light source 300.

FIG. 12 is a perspective view of the air sterilization chamber illustrated in FIG. 11, with the end flaps 310 in three different positions. In particular, in FIG. 12a, the flaps 310 are in the open position. In the open position air flows through the sterilization chamber 300, via the inlet aperture 330 and the outlet aperture 340.

In FIG. 12b the end flaps 310 are in a partially closed position. As discussed above, the end flaps 310 are pivotably connected to the sterilization chamber 300 so that they may be moved between an open (FIG. 12a) and a closed (FIG. 12c) position. In the particular embodiment of FIG. 12, the end flaps 310 are hinged to the air sterilization chamber 300 and pivoted around the hinge in order to open and close. The end flaps 310 may be propelled by a solenoid actuator or any other means of moving the flap that is known in the art. One of skill in the art will also recognize that any number of connection mechanisms are available to accomplish the same functions. In general, for all embodiments described, any device that moves a reflective material over openings in the sterilization chamber while the light source is emitting light may advantageously increase the fluence within the chamber. Alternatively, in any embodiment, the openings for air may be on any surface of the sterilization chamber 300, such as the top and bottom or top and side, for example.

In FIG. 12c the end flaps 310 are in the closed position, substantially covering the inlet aperture 330 and the outlet aperture 340, so that substantially no air may enter or exit the chamber. Likewise, if all of the inner surfaces of the air sterilization chamber 300 (e.g. those facing the emitter 320) comprise a reflective material, the fluence within the sterilization chamber will be improved.

FIG. 13a-13c are perspective views of an embodiment of an air sterilization chamber 300 where the end flaps 310 slide up and down the walls of the sterilization chamber 300 and are shown in three different positions. In particular, in FIG. 13a, the flaps 310 are in the open position. The flaps are parallel to the side wall of the sterilization chamber 300. With both the end flaps in the open position air flows through the sterilization chamber 300 via the inlet aperture 330 and the outlet aperture 340.

In FIG. 13b the end flaps 310 are in a partially closed position. As discussed above, the end flaps 310 slide along the wall of the sterilization chamber 300 so that they may be moved between an open (FIG. 13a) and a closed (FIG. 13c) position. In the particular embodiment of FIG. 13, the end flaps 310 are attached with a mechanism that allows them to slide up and down the wall of the sterilization chamber 300. The end flaps 310 may be propelled by a solenoid actuator or any other means of moving the flap that is known in the art. One of skill in the art will also recognize that any number of connection mechanisms are available to accomplish the same functions.

In FIG. 13c the end flaps 310 are in the closed position so that substantially no air may enter or exit the chamber. Likewise, if all of the inner surfaces of the air sterilization chamber 300 (e.g. those facing the emitter 320) comprise a reflective material, the fluence within the sterilization chamber will be improved.

FIGS. 14a-14c are perspective views of a configuration in which the moveable ends comprise blinds having multiple slats 605 that may be raised and lowered, similar to the movement of Roman blinds. FIGS. 14a-14c are perspective views of a first embodiment of an air sterilization chamber with the multiple interconnected slats 605 in three different positions. In particular, in FIG. 14a, the interconnected slats 605 are in the open position. In the open position air flows through the sterilization chamber 300 via the inlet aperture 330 and the outlet aperture 340.

In FIG. 14b the interconnected slats 605 are in a partially closed position, such that less air is allowed through the inlet aperture 330 and outlet aperture 340 when compared to the open position illustrated in FIG. 14a. The interconnected slats 605 may be further lowered so that the slats 605 cover the inlet aperture 330 and the outlet aperture 340 in a closed position illustrated in FIG. 14c. In one embodiment, the interconnected slats 605 comprise a reflective material on an inner surface, i.e., facing the emitter 320, so that the light in the chamber 300 is reflected within the chamber 300, advantageously increasing the fluence within the chamber 300. The interconnected slats 605 may be propelled by a solenoid actuator or any other means of moving the slats 605 that is known in the art.

Figures 14D, 14E, 14F:
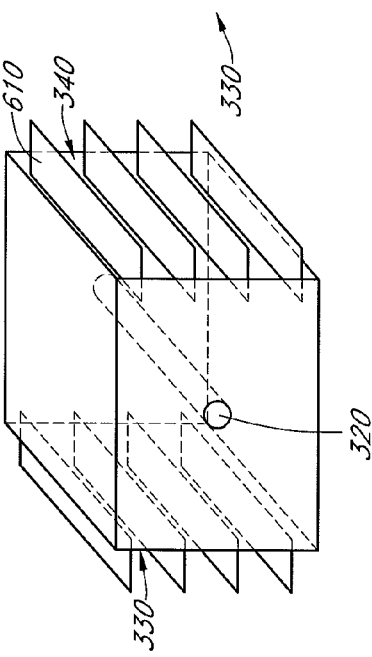
FIG. 14d is a perspective view of another embodiment of an air sterilization chamber in which the moveable ends comprise multiple slats, where the multiple slats are in the open position.
FIG. 14e is a perspective view of an embodiment of an air sterilization chamber in which the moveable ends comprise multiple slats, where the multiple slats are in the partially closed position.
FIG. 14f is a perspective view of an embodiment of an air sterilization chamber in which the moveable ends comprise multiple slats, where the multiple slats are in the closed position.

FIGS. 14d-14f are perspective views of a configuration in which the moveable ends comprise blinds having multiple slats like Venetian blinds. FIGS. 14d-14f are perspective views of the second embodiment of an air sterilization chamber with the multiple slats, referred to herein as Venetian blinds, 610 in three different positions. In particular, in FIG. 14d, the Venetian blinds 610 are in the open position. In the open position air flows through the sterilization chamber 300 via the inlet aperture 330 and the outlet aperture 340.

In FIG. 14e the Venetian blinds 610 are in a partially closed position. As discussed above, the Venetian blinds 610 pivot about supports connected to the sterilization chamber 300 so that they may all move between an open (FIG. 14a) and a closed (FIG. 14c) position. In the particular embodiment of FIG. 14, the Venetian blinds 610 pivot about supports when they open and close. The Venetian blinds 610 may be propelled by a solenoid actuator or any other means of moving the flap that is known in the art. One of skill in the art will also recognize that any number of connection mechanisms are available to accomplish the same functions.

In FIG. 14c the Venetian blinds 610 are in the closed position so that substantially no air may enter or exit the chamber. Likewise, if all of the inner surfaces of the air sterilization chamber 300 (e.g. those facing the emitter 320) comprise a reflective material, the fluence within the sterilization chamber will be improved.

Figure 15A:
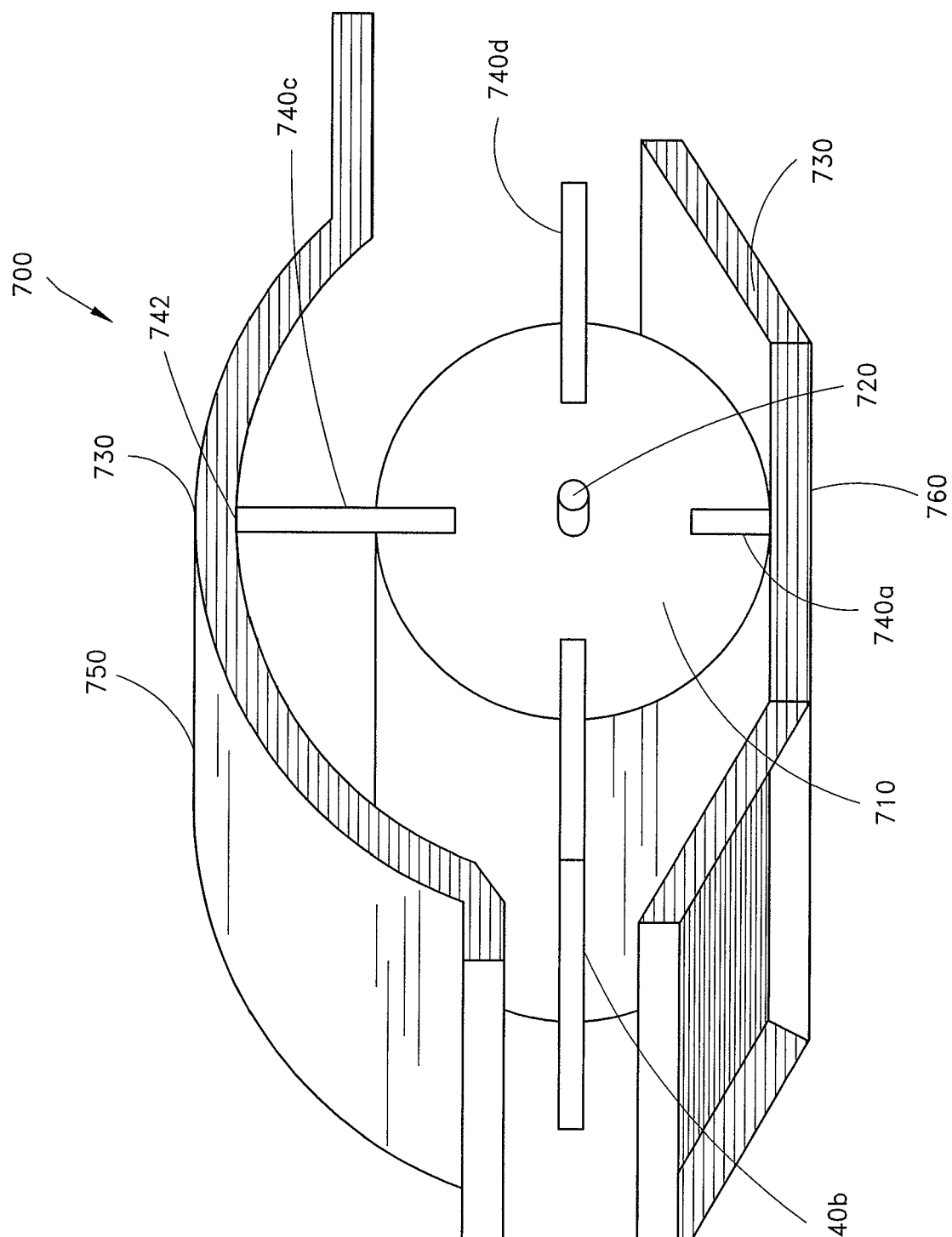
FIG. 15A is a perspective view of a rotating drum inlet/outlet valve configured to move air in a first direction while preventing light from moving through the valve in a second direction.

FIG. 15A is a perspective view of rotating drum configuration that can be placed at the inlet and/or outlet of an air sterilization chamber in order to move air in and out of the chamber while preventing light from exiting the chamber. A rotating drum unit 700 may be placed on an input and/or output of a sterilization chamber. In the embodiment of FIG. 15A, the ratio (α) of non-reflecting area to total area can be minimized without needing to synchronize the opening and closing of flaps to the flashing of a lamp. In addition, the embodiment of FIG. 15A may also provide increased efficiency (e.g. lower power requirement for specific kill) in sterilization chambers that use steady state UV sources, and may therefore improve the efficiency of any type of sterilization chamber that uses ultraviolet light for killing microorganisms.

In the exemplary embodiment of FIG. 15, the valve 700 comprises a rotating drum 710 mounted on an axle 720 inside a housing 730. In the embodiment of FIG. 15A, the rotating drum 710 is mounted substantially flush against a surface 760 of the housing 730 while the drum is distant from a surface 750 of the housing 730. The valve 700 is configured to allow air to flow in only one direction, between the rotating drum 710 and the upper surface 650, depending on the direction of rotation of the rotating drum 710.

The drum may be rotated by the force of the air flow alone. This will result in a slight air pressure drop across the drum inlet and exit, as the air flow must provide energy to overcome drum friction. A small motor may rotate the drum instead, providing enough rotational energy to reduce or eliminate the air pressure drop as needed.

In one embodiment, the drum 710 further comprises a plurality of retractable vanes 740 (including 740a, 740b, 740c, and 740d in FIGS. 15A-15D) configured to extend different amounts from the outer surface of the drum 710 at different rotational location of the drum 710. In operation, the drum 710 rotates about the axle 720 and the vanes 740 retract and extend so that substantially no light may pass from one side of the valve 700 to the other. In an advantageous embodiment, all surfaces of the rotating door configuration comprise a reflective material in order to increase the fluence within an attached sterilization chamber. Thus, from the side in which the UV radiation is created, all surfaces comprise reflecting material and, in effect, the chamber has no open area. Prototypes of these rotating vane devices have been tested and they have very low resistance to air flow.

Figure 15C:
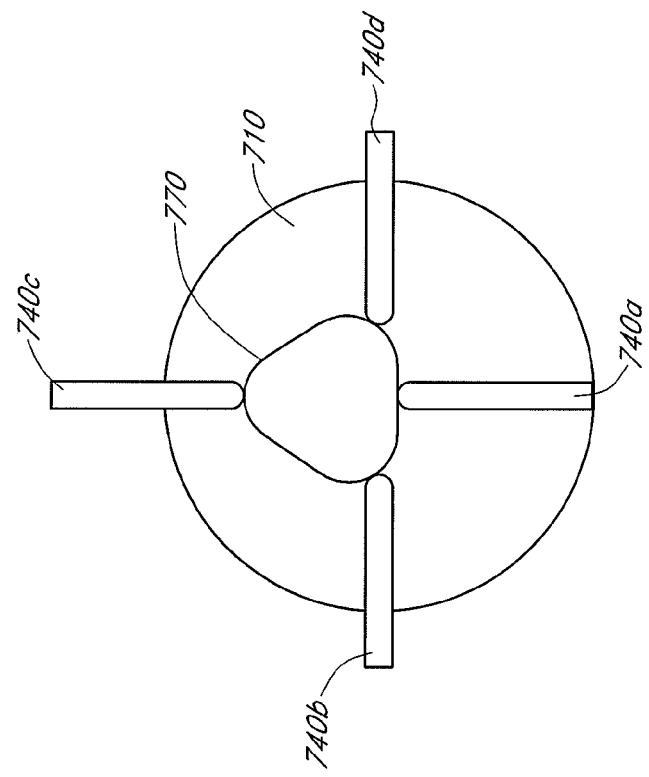
FIGS. 15B-15D are cross section views of the rotating drum inlet/outlet valve having alternative configurations of retractable vanes.
Figure 15B:
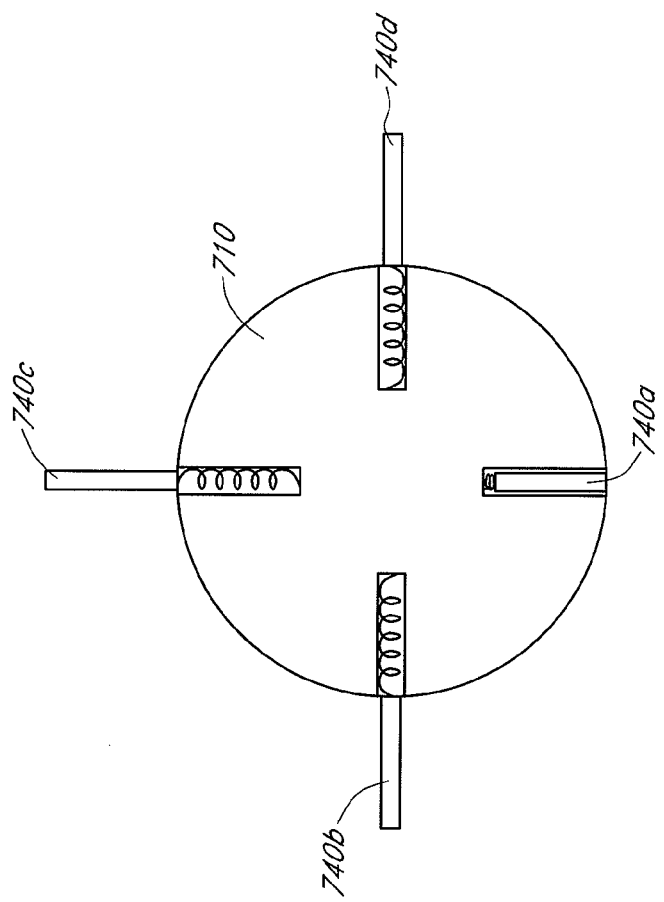

In the embodiment of FIG. 15B, each of the vanes 740 are spring loaded so that when no pressure is applied to the distal end of the vane, the vane is in an extended position (in FIG. 15B, vane 740b is in the extended position), and when pressure is applied to the distal end of the vane, the vane retracts into the body of the drum 710 (in FIG. 15B, vane 740a is in the retracted position). For example, with the drum 710 rotated to the position illustrated in FIG. 15, vane 740d is in an extended position, but as the drum 710 rotates clockwise the vane 740d will come in contact with the lower surface 760 the vane 740d will begin to retract. The vane 740 may be completely retracted, with the spring compressed, when the drum is substantially flush against the housing, such as vane 740a in FIGS. 15A and 15B. In one embodiment, the distal end of the vanes 740 (e.g end 742 of vane 740c) may be rounded so that when the vane is in contact with the lower surface 760 of the housing 730 the vane may more smoothly move along the surface.

In the embodiment of FIG. 15C, the plurality of retractable vanes 740 may be extended and retracted by a cam mechanism 770 inside the drum 710. The cam mechanism 770 remains stationary as the drum 740 and vanes 740 rotate around the cam mechanism 770. Because of the non-circular shape of the cam mechanism, as each of the vanes rotates around the cam mechanism, they are extended and retracted from the surface of the rotating drum. For example, in FIG. 15C, the vane 740a is substantially completely retracted inside the drum 710 and the vane 740c is substantially extended from the surface of the drum 710.

Figure 15D:
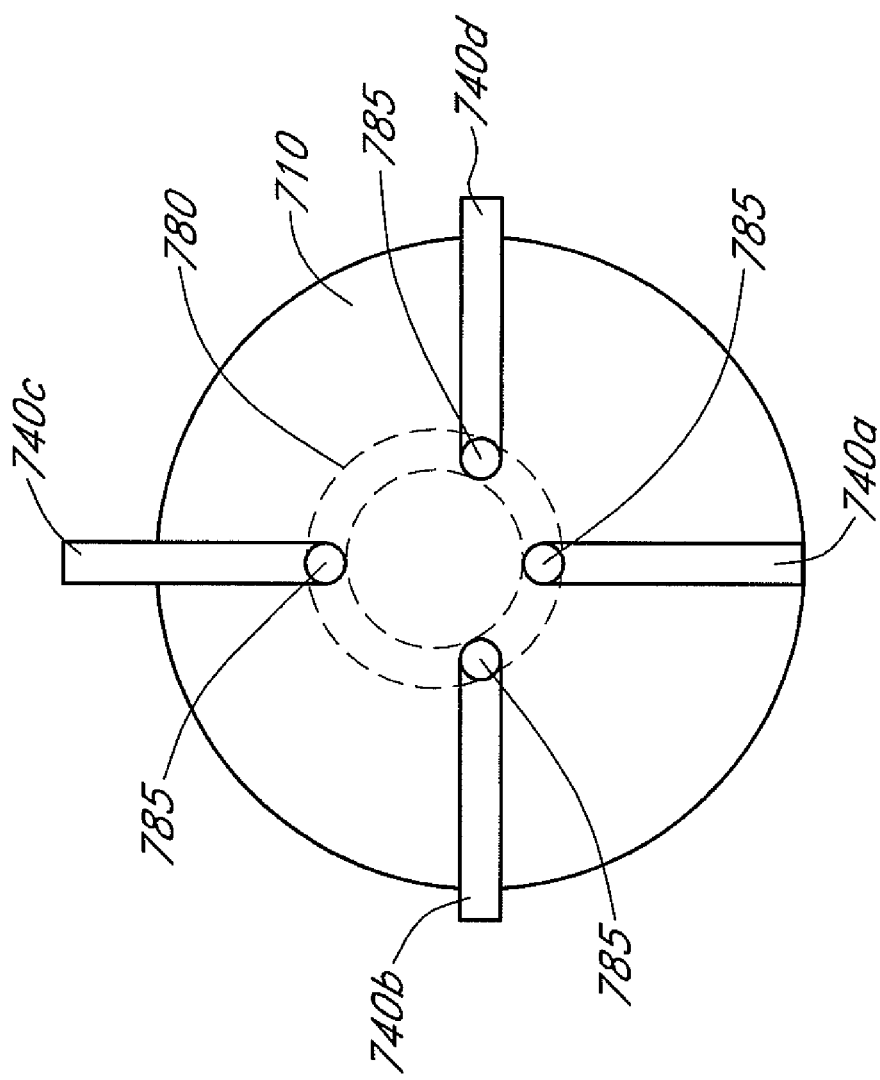

In the embodiment of FIG. 15D, the plurality of retractable vanes 740 may each have a pin 785 or set of pins at the near and/or distal ends that ride in an eccentric groove 780 in the rotating drum 710 side walls. The grooves are circular or any appropriate shape, and are centered on the side walls about an axis that is largely the central axis of the housing 730. As the drum 710 rotates, the pins 785 riding in the groove 780 generate a radial force on the vanes 740, extending or retracting them depending on the vane position and the drums' direction of rotation. The pins may be rotating bearings or ball bearing, such as those used in roller skates, to reduce the friction of the device.

One of skill in the art will recognize that the rotating door configuration 700 may be constructed in many different manners in order to achieve substantially equivalent results. For example, the number of vanes 740 may be increased or decreased according to the specific needs of the sterilization chamber. In addition, the drum may be shaped differently, such as polyangularly shaped, for example.

Figure 16:
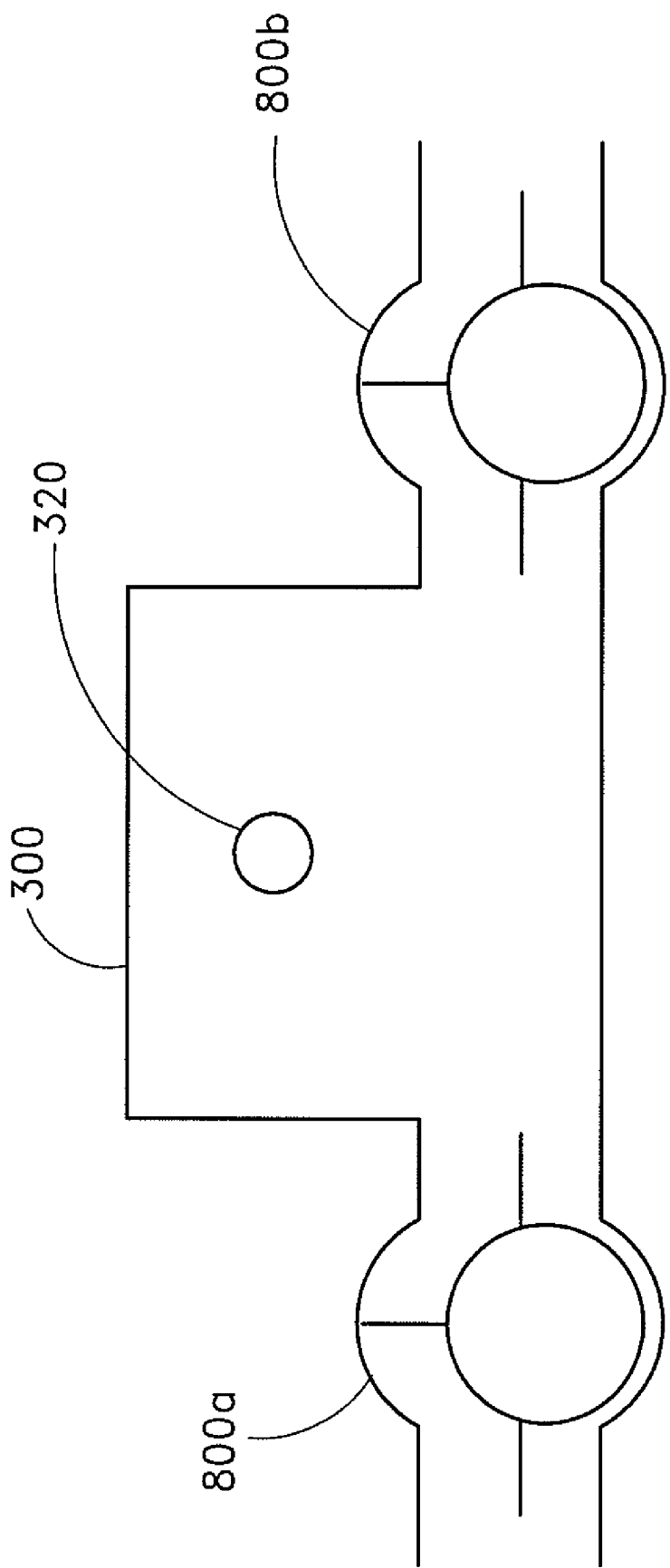
FIG. 16 is a schematic illustrating a cross section of a sterilization chamber coupled between an inlet rotating drum and an outlet rotating drum.

FIG. 16 is a schematic illustrating a cross section of a sterilization chamber 300 coupled between an inlet rotating drum 800a, an outlet rotating drum 800b. In one embodiment, the rotating drums 800a and 800b have substantially the same structure as illustrated in FIG. 15. FIG. 16 shows a rotating drum mechanism located at the inlet to a sterilization module and a valve located at the outlet of the sterilization module. Prototypes of these rotating vane devices have been tested and they have very low resistance to air flow.

Figures 17A, 17B:
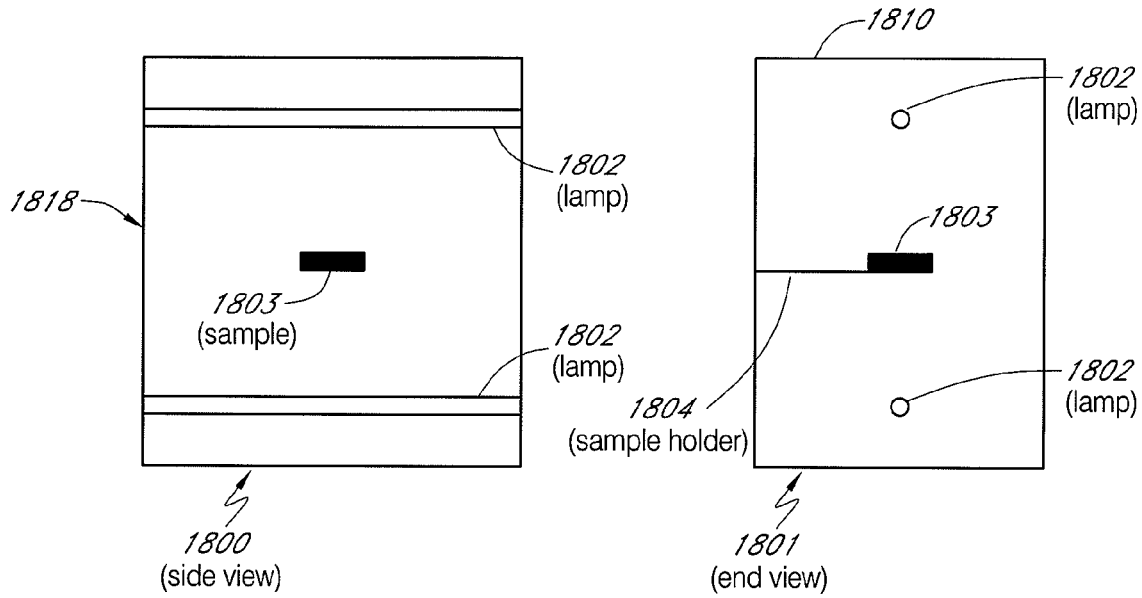
FIG. 17A is a side view and FIG. 17B is an end view of a sample exposure system that may be implemented in a lamp box multiplier.

In another embodiment, industrial process applications of UV radiation exposure, such as UV curing systems and sterilization of packaged components, are improved by the enhanced efficiency of the inventions described herein. FIG. 17A is a side view and FIG. 17B is an end view of a sample exposure system that may be implemented in accordance with some embodiments of the invention. As illustrated in FIG. 17A, two lamps 1802 are located within the lamp box multiplier 1810. The lamps 1802 may be flash lamps, medium pressure mercury arcs or germicidal lamps, for example. In one embodiment, a sample holder having a thin frame (not shown) holds a sample 1803 within the lamp box multiplier 1810. The sample holder is advantageously configured to avoid absorption of photons. The sample 1803 can be semi-transparent or opaque.

Example

The sample is assumed to be a completely opaque rectangle, 5"×1.5", thin, with two sides. The lamps 1802 are assumed to be flash lamps 9" long, and 9 mm in diameter and operate at 65 joules/inch and emitting 50% of the stored energy as light.

The results vary with the size of the particular lamp box multiplier 1810. In the table below, the results for a square lamp box multiplier 1810 (referred to generally as a "box") of different sizes are compared for CWUV lamps.

| Box Side | Multiplier M | Flux on sample |
| --- | --- | --- |
| 10" | 26 | 3.96 joules/$cm^2$ |
| 20" | 57 | 2.14 joules/$cm^2$ |
| 30" | 73 | 1.23 joules/$cm^2$ |

Figure 18:
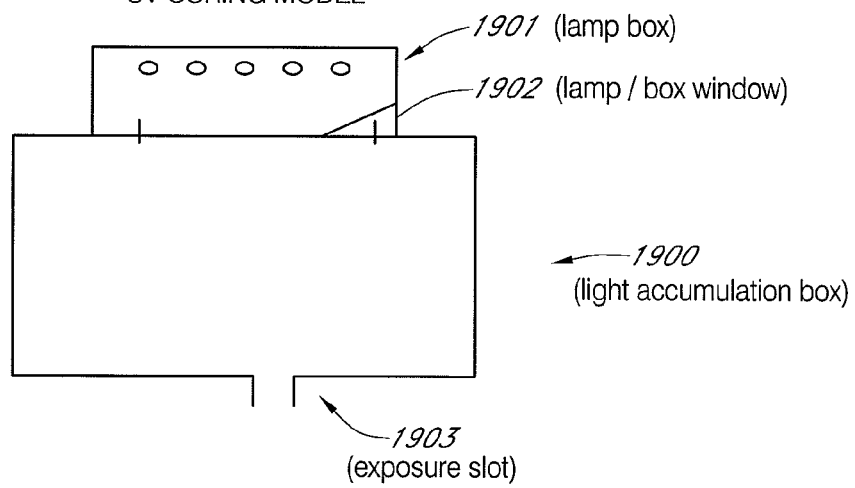
FIG. 18 is a cross-sectional side view of a light accumulation box attached to a lamp box.

Another embodiment is for UV curing. By combining the power of less expensive germicidal lamps in a multiplying box, high intensity exposures of germicidal 254 nm radiation can be achieved, intensities comparable to microwave lamps or medium pressure mercury lamps are possible. Such a chamber is shown in FIG. 18. FIG. 18 is a cross-sectional side view of a light accumulation box 1900 attached to a lamp box 2001. The light accumulation box 1900 receives power from multiple germicidal lamps mounted in lamp box 1901 which transmit light through a lamp/box window 1902. An exposure slot 1903 releases the light and exposes a surface or a conveyer belt located directly underneath. The lamps can also be located in the light accumulation box 1900. In the case of one flash lamp as described above, the following exposure can be achieved.

Figure 19:
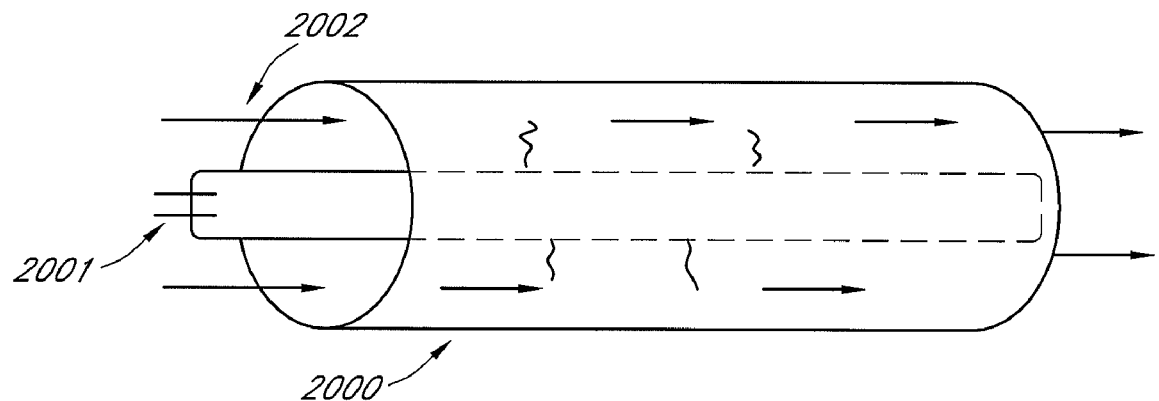
FIG. 19 is a perspective view of a photochemical reactor.

It has been found that with a lamp as described above with dimension of 7"×7"×12", and with a slot width of 1" the flux through the exposure slot 1903 is 2.63 joules/$cm^2$. With a slot width of 1.5" the flux through the exposure slot 1903 is 1.9 joules/$cm^2$ In another embodiment, flux multiplication is used to enhance photochemical reactions in air. FIG. 19 is a perspective view of a photochemical reactor 2000. It consists of a reactor chamber 2100, a light source 2101 and a flowing chemical mixture, either in air or in a fluid 2102. Typically, photochemical industrial reactors have been successful when the reaction cross sections are sufficiently large for significant reactions to occur in the chamber.

Figure 20:
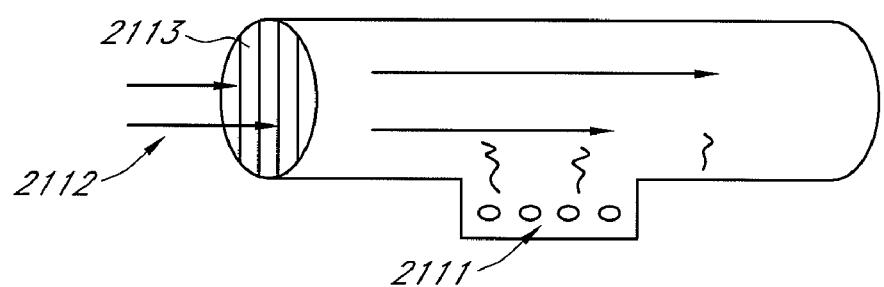
FIG. 20 is a perspective view of a light box photochemical reactor, including reflecting walls and reflecting end slats.

FIG. 20 is a perspective view of a light box photochemical reactor 2112, including reflecting walls and reflecting end slats 2113. In one embodiment the slats 2113 partially close the chamber as in the case of air applications. The flowing chemical mixture is denoted by 2112.

Figure 21:
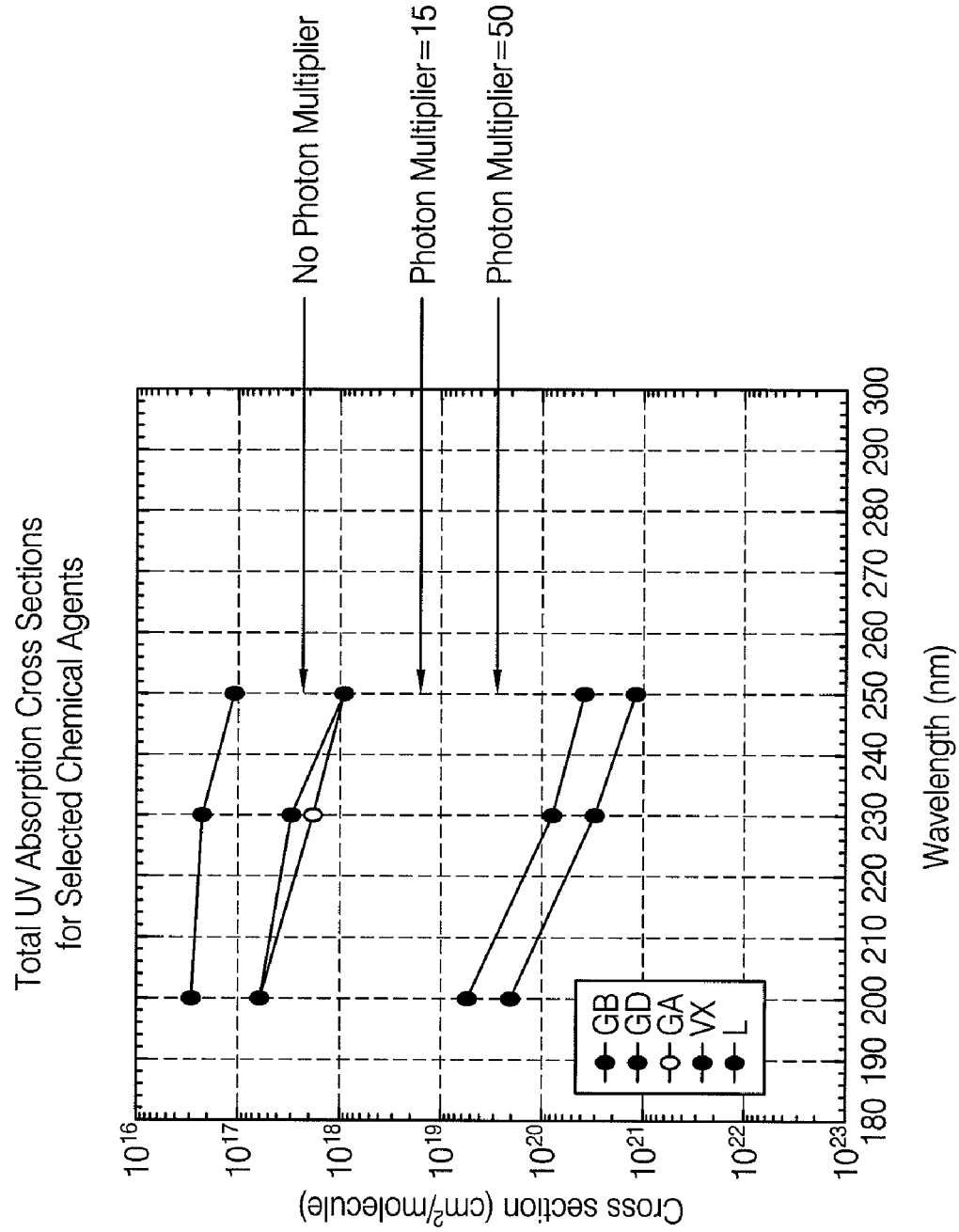
FIG. 21 is a line graph illustrating the total UV absorption for selected chemical agents.
Figure 22:
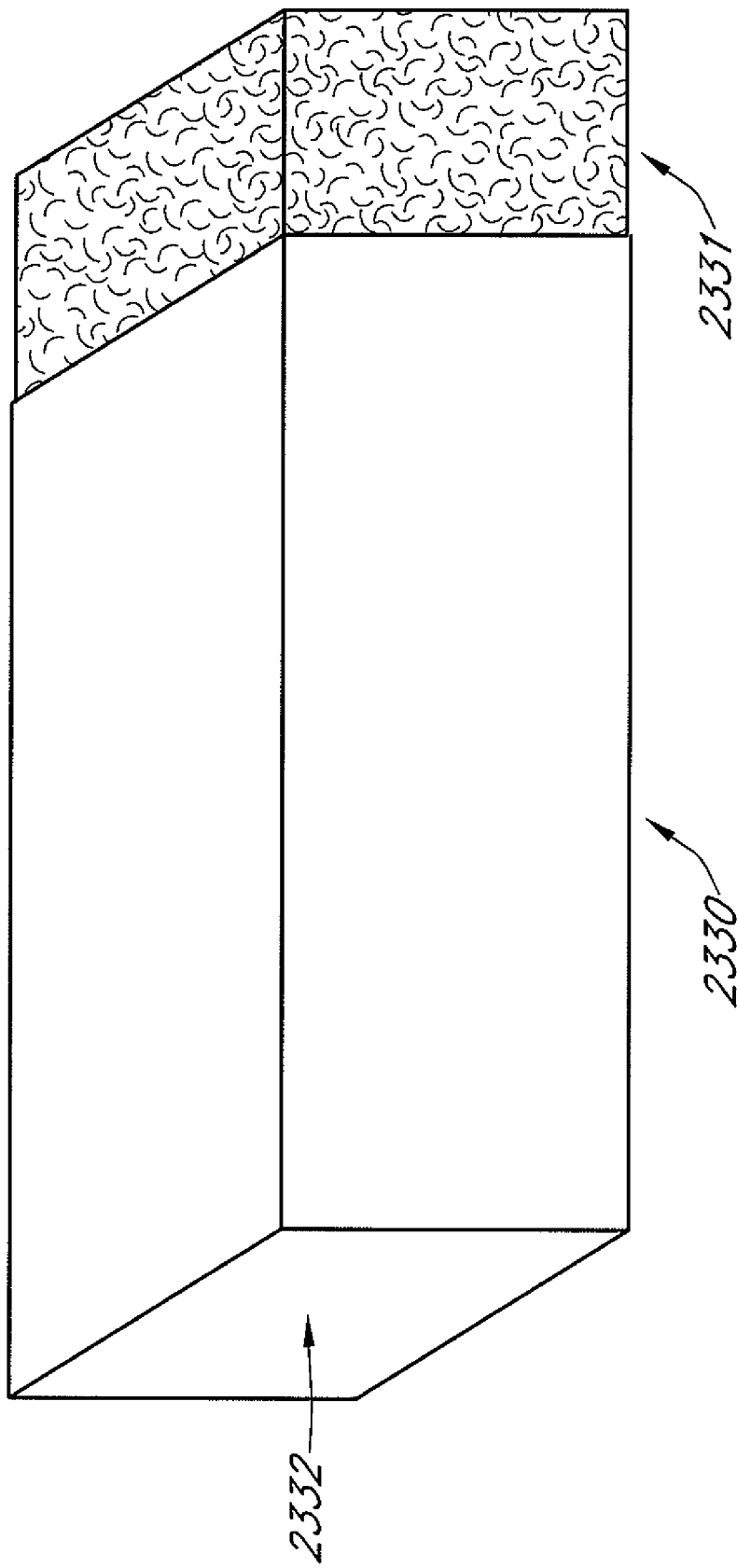
FIG. 22 is a perspective view of a light multiplying box with a flow of chemicals in air or solvent that has a system of photocatalysts intersecting the flow stream.

In an advantageous embodiment the flux of the light in the light box photochemical reactor 2112 is multiplied by the multiplier, M, as defined above. The light box photochemical reactor 2112 can be applied to a greater range of chemical processes to have industrial significance. This can be illustrated by examining the effect of the chamber on processing of chemical agents GB,GD,GA,VX, and L. FIG. 21 is a line graph illustrating the total UV absorption for selected chemical agents. In FIG. 21, the cross sections for UV interaction of the agents are shown as a function of UV wavelength. In a conventional photon multiplier, the smallest cross section that can be applied is $2\times10^{-18}$ cm. This level is indicated by an arrow in the FIG. 21, labeled "No Photon Multiplier". In the light multiplying box, the fraction of particles that react can be described as follows:

$$\text{Fraction Remaining} = \frac{F_0\left(1 - e^{\frac{-xM}{l_0}}\right)}{n_{agent}x}$$

$$F_0 = \frac{\text{Photons}}{\text{cm}^2}$$

$$l_0 = \frac{1}{n_{agent}\sigma_{agent}}$$

$x$ = Path Length Between Walls $\sigma_{agent}$ = cross section of agent $n_{agent}$ = number density of agent Thus, with a multiplier of 15, typical of a light multiplying box with reflectivity equal to 0.99 and an end 20% open the effective cross section becomes $1.3\times10^{-19}$ $cm^2$. A photon multiplier of 50, which is also achievable with present systems, drops the effective cross section to $5\times10^{-20}$ $cm^2$. Through the use of a photochemical reactor, as described above, higher reflectivities are possible (0.998 and higher) and even further advances in effective cross section size can be made.

In another embodiment, a photon multiplication chemical enhancer is used in combination with photocatalyst systems. FIG. 22 is a perspective view of a light multiplying box 2330 with a flow of chemicals in air or solvent 2332 that has a system of photocatalysts 2331 intersecting the flow stream.

As an example of the advantage of this synergetic combination of light box and photocatalyst:

The agent VX has been studied with Ti $O_2$ photocatalyst and it has been found that the active sites on the photocatalyst are covered by the VX, diminishing the effectiveness. If the direct photochemistry can break up the agent into smaller fragments, then they may be more favorably reacted on the photocatalyst surface.

FIGS. 23-27 depict an alternate embodiment of an air sterilization chamber 2400. With respect to FIG. 23, it can be seen that the air sterilization chamber 2400 comprises a duct body 2410 having an upper panel 2412, side panels 2414 and 2416, and a base panel 2418. Although referred to herein as distinct panels, it will be understood that a particular side of the duct body may comprise multiple panels joined together, or that a single panel may be bent to serve as multiple sides of the duct body. It will also be understood that, while the illustrated embodiment is positioned such that the air flows through in a generally horizontal direction, as shown by the arrow, the terms upper, lower, and side refer only to the illustrated orientation for the purposes of description, and the air sterilization chamber may be oriented in any direction.

At either end of the duct body 2410, end components permitting air flow therethrough are positioned. In the illustrated embodiment, these end components comprise end panels 2420 having diffuse, highly reflective interior surfaces. In certain embodiments, the panels 2420 may be held in place against a gasket plate and a gasket retained therebetween, to form an airtight seal and ensure that all air flows through, rather than around, the end panels.

In one embodiment, the end panels 2420 comprise a perforated metal panel and a diffuse, highly reflective coating on the interior surface, although materials other than metal may be used in place of the metal plate. DRP is particularly well suited for use, as a sheet of DRP can be adhered to one side of a perforated metal sheet, and the DRP sheet be perforated at locations overlying some or all of the perforations in the metal panel. In particular embodiments, the DRP sheet may comprise a DRP sheet about 1 mm in thickness, but in other embodiments the DRP sheet may be thicker or thinner than 1 mm.

The size of the apertures in end panel may vary depending on the application, but in one embodiment the apertures comprise substantially circular holes having diameters of about 0.5 inches. In other embodiments, however, the size and shape of the apertures may vary. In certain embodiments, the open area of the end panels is between 15% and 20% of the total area of the end panel. It will be understood that this ratio may vary depending on the embodiment. This ratio represents a balance between the light flux within the chamber (which will decrease as the open area increases due to light escaping through the apertures) and pressure drop (which will increase as the open area decreases as air flow is inhibited by the reduction in open area through which the air can flow).

It will be understood that the desired size of the apertures may vary depending on factors such as the size of the sterilization system, the desired number of apertures, and the shape of the apertures. For an embodiment in which the end plate has an area A exposed to the interior of the duct, the fraction of open area in the exposed portion of the end plate is given by F, and the number of apertures in the end plate is given by N, the diameter d of circular apertures which would provide the desired properties is given by setting the value for F equal to the number of apertures N multiplied by the area of the apertures $A_h$, divided by the exposed area of the end plate A. Because the area of circular apertures is a function of the diameter d, and all other values have been provided, the desired value of d may be calculated as shown below:

$$F = \frac{NA_H}{A}$$

$$A_H = \frac{\pi d^2}{4}$$

$$d = 2\sqrt{\frac{FA}{N\pi}}$$

In certain embodiments, for large scale sterilization systems, a diameter of between 0.5 inches and 2.5 inches may be desirable, but it will be understood that the number may vary significantly if other factors, such as the desired number of apertures, are modified. Such a process may also be used to define desired dimensions of other apertures, as well. For example, in certain embodiments it may be desirable to utilize slot-shaped apertures or oval-shaped apertures, and the above process may be used to, for instance, determine a proper width for apertures given a desired width, or to define an appropriate relationship between aperture width and aperture height given the other features.

The distribution of the apertures may also vary across the width and height of the end panel. For example, the aperture density may be greater near the edges of the end panel with fewer holes near the center of the end panel. Such a configuration will serve to equalize air flow throughout the air sterilization system, as the air would otherwise flow at a greater rate through the central portion of the end panels and air ducts due to shear forces near the edge walls of the system. In one embodiment, this configuration can be achieved by providing a perforated metal panel having the desired aperture distribution and perforating the DRP sheet over each of the apertures. In another embodiment, this configuration can be achieved more simply by providing a metal panel having a regular aperture distribution and perforating it only over particular apertures, so as to produce the desired aperture distribution, as the unperforated DRP will inhibit air flow through the other apertures. This embodiment may simplify the fabrication process.

Again, although the illustrated embodiment is described as having perforated end panels, any suitable component may be used in place of the above described end panel. In particular, any of the designs previously discussed above may be incorporated into the air sterilization chamber, or any combination thereof. For example, the end panels may comprise offset slats, or movable components. In other embodiments, the end panels may comprise expanded PTFE or other reflective elements, and may be suspended within a frame.

It can also be seen that the exterior of the duct housing may comprise additional housing members which may provide partially or fully contained compartments such as compartments 2430. These compartments may be used to contain and protect electrical or other components. For example, compartments 2430 may provide containment and protection for the electrical connections with and between UV lamps on the interior of the air sterilization chamber. An access port, such as hinged access port 2432, may also be provided for easy access to the interior of the duct housing.

In certain embodiments, the air sterilization chamber may comprise electronics in the form of an electrical panel contained within a large exterior compartment 2434. The exterior compartment may comprise external controls and connection ports 2456, which in certain embodiments may include on/off switches or other controls. In embodiments in which connection ports are provided, such connection ports may be used to receive control instructions from an external system, or may be used to output information to an external system regarding the status of the air sterilization chamber.

In certain embodiments, these exterior compartments are preferably isolated from the interior of the duct housing by air tight seals, such that air can only enter and exit the interior of the duct housing via the end panels 2420, ensuring that air which passes through the air sterilization chamber has traversed the entire length of the chamber, ensuring extended exposure to the UV radiation within.

Figure 25:
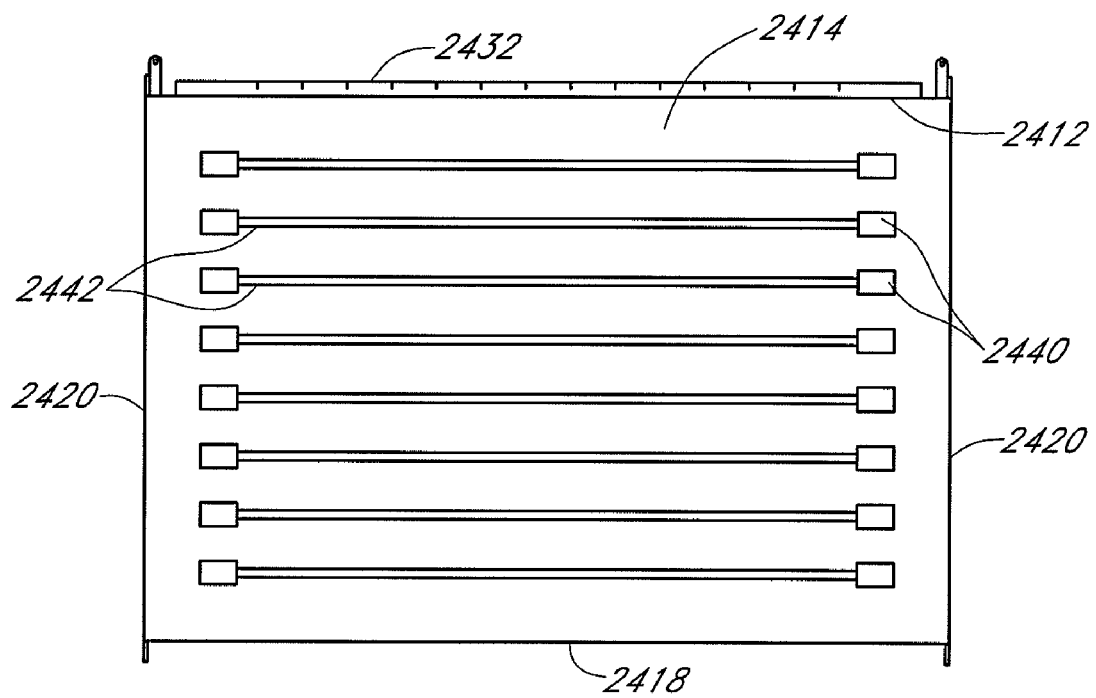
FIG. 25 is a side cross-section taken along the line 25-25 of FIG. 23.

FIG. 25 is a side cross-section of the interior of the air sterilization unit. As discussed with respect to previous embodiments, the interior surfaces of the panel 2412, 2414, and 2416 are coated with a diffuse reflector having a very high reflectivity. As illustrated by the equations above, and in particular equation 2, it will be understood that for very high levels of reflectivity, even a small increase in the reflectivity of the interior surface may result in a substantial increase in the multiplier producing high flux density within the sterilization chamber.

The interior surface of side panel comprises UV lamp fixtures configured to retain and power UV lamps 2442. These UV lamp fixtures may advantageously be coated in a diffuse, highly reflective material, similar to the interior surfaces of the duct housing. In a particular embodiment, the UV lamp fixtures and associated wiring and other components may be covered by and retained within housing structures 2440. These housing structures 2440 can have smooth exterior surfaces, facilitating the coating of these exterior surfaces in expanded PTFE as compared with coating an exposed fixture and wiring.

The illustrated UV lamp fixtures are positioned to retain the lamp in a substantially horizontal position extending generally parallel to the air flow through the air sterilization unit. The positioning of these UV lamps in a direction parallel to and at the periphery of the air flow through the chamber helps avoid a drop in air pressure due to impedance of the flow by the UV lamps, by minimizing their profile in the direction of the air flow. In certain embodiments, the pressure drop within the apparatus may be less than 0.5 w.i.g., and in further embodiments may be less than 0.4 w.i.g. or less than 0.3 w.i.g. The housing structures 2440 surrounding the lamp fixtures may be contoured or otherwise shaped to minimize resistance to air flow through the chamber. It is often also easier to service the UV lamps in the illustrated position, as the interior of the duct housing can be accessed from the hinged access port above. It will be understood, however, that the use of diffuse reflective material enables high and uniform light flux throughout the chamber wherever the lamps are located.

In embodiments which include an array of UV lamps, it will be understood that the array of UV lamps can be used to provide redundancy, such that if one or more of the lamps burns out or otherwise fails, the remaining UV lamps which are still functioning can provide sufficient light flux throughout the chamber to maintain an acceptable level of sterilization. Downtime necessitated by UV lamp replacement can thus be minimized. The easy access to the interior of the sterilization system via the access port also facilitates replacement of UV lamps if such replacement becomes necessary, further minimizing system downtime. Furthermore, in embodiments in which UV lamps are secured to a single interior surface of the duct, the risk of damage to the lamps or fixtures due to impact with or deformation of the sterilization system is minimized, as deformation of or movement of one interior surface relative to another may cause undesirable stresses in a UV lamp secured between two different interior surfaces. By securing a particular UV lamp to only a single surface, the likelihood of such potentially damaging stresses can be minimized.

In the embodiment of FIG. 25, the UV lamps extend almost the entire length of the air sterilization unit. However, the lamps need not extend the entire length of the chamber in order to ensure high and constant light flux throughout the chamber, as discussed above. The size and number of lamps may thus be dependent upon the amount of light generation desired for a given application. In embodiments in which a longer flow path through the UV radiation is desired, such as if the air flow rate is high, or additional exposure is deemed necessary, longer UV lamps 2442 may be used, or an additional bank of UV lamps may be provided. In an alternate embodiment, the air sterilization unit may be used in a modular manner, wherein multiple air sterilization units are provided in series. In alternate embodiments, the position of the lamps may be moved while still providing substantially uniform light flux throughout the chamber, due to multiple reflections from the diffuse reflective surfaces. So long as care is taken to avoid light loss at or through the end panels, and a sufficiently diffuse and reflective material is used on the internal surfaces, the effect of the position of the lamps on the strength and regularity of the UV flux throughout the chamber can be minimized. It will be understood that in certain embodiments, the UV lamps 2442 may be positioned within recesses in the walls of the chamber, similar to embodiments previously discussed, although such an embodiment may add additional complexity to the manufacturing process.

Figure 23:
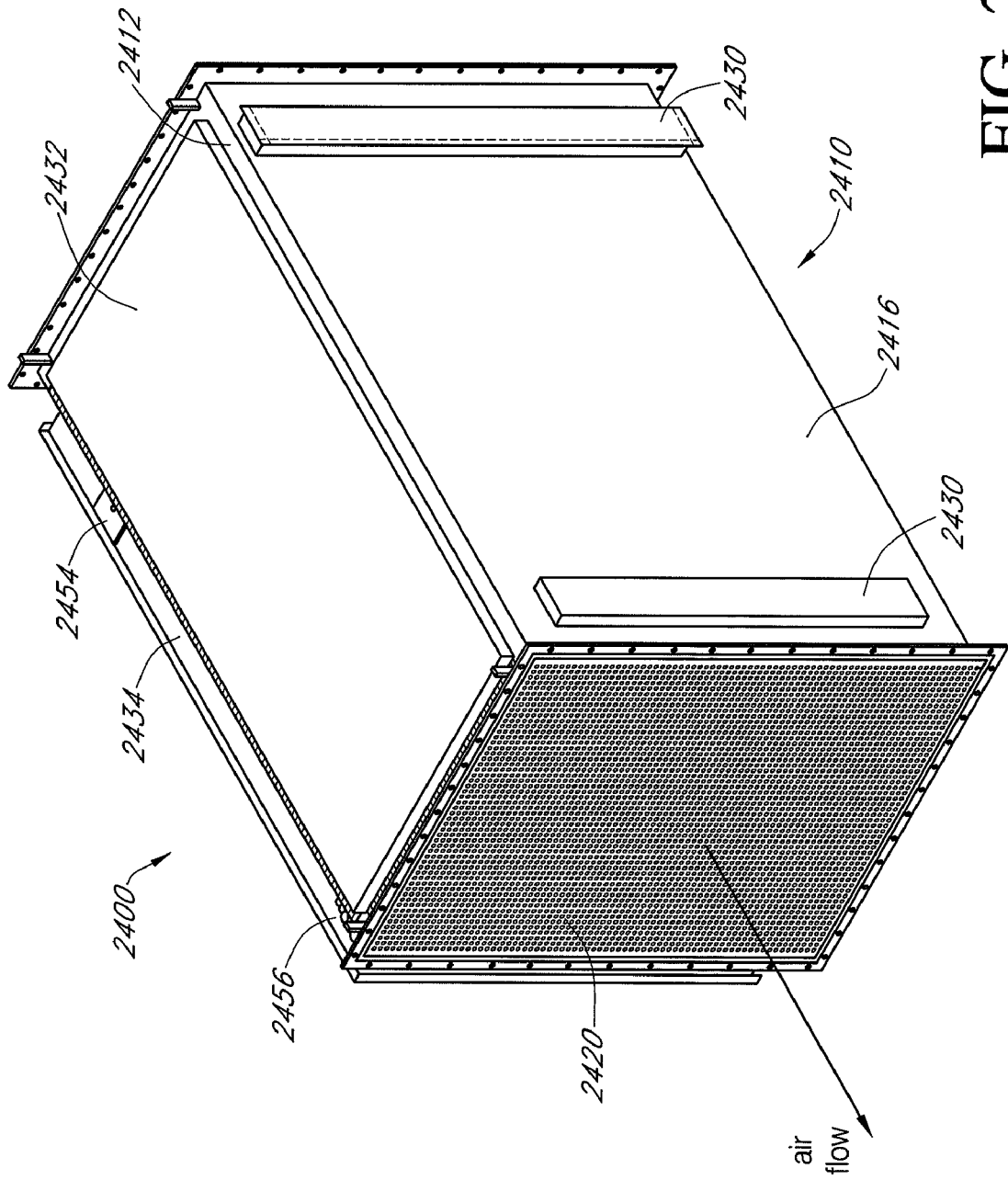
FIG. 23 is a perspective view of an alternate embodiment of an air sterilization chamber.
Figure 24:
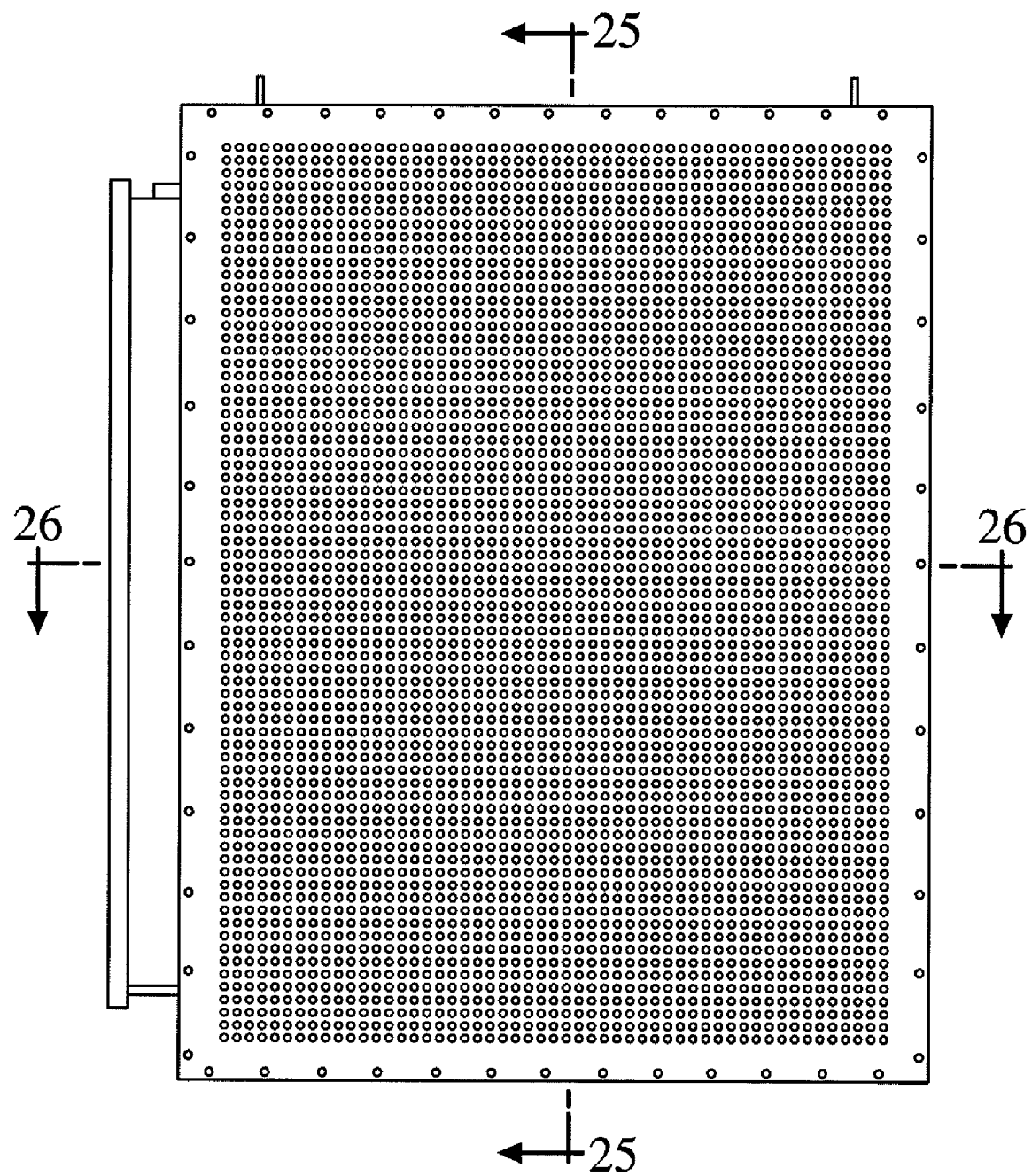
FIG. 24 is a front elevation view of the air sterilization chamber of FIG. 23.
Figure 26:
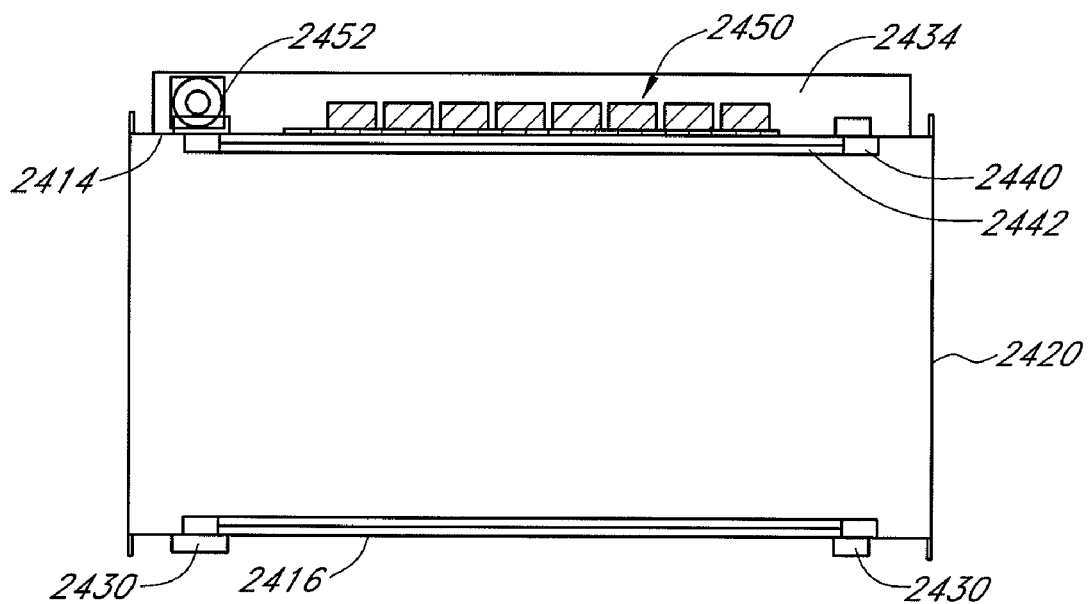
FIG. 26 is a top cross-section taken along the line 26-26 of FIG. 23.

In FIG. 26, the interior of the exterior compartment 2434 can be seen. In particular, it can be seen that the exterior compartment comprises an electrical panel which may be configured, for example, to control the air sterilization device, as well as to communicate with external systems or devices regarding the state of the air sterilization device. The exterior compartment 2434 may comprise a lower fan 2452 which may be located within or adjacent to an aperture in the bottom surface of the exterior compartment. This fan, in cooperation with an upper fan 2454 located within or adjacent an aperture in the upper surface of the exterior compartment (see FIGS. 23 and 27), provides air flow through the compartment. This cooling air flow may cool the electrical components, preventing damage from overheating as well as minimizing conductive heat transfer into the interior of the duct housing. Advantageously, the fans are positioned at opposite sides of the exterior compartment, so that the air flow moves across the electrical panel and any other components within the exterior compartment. The fans 2452 and 2454 may also be configured to blow air in an upward direction so as to facilitate the removal of warmer air from the exterior compartment.

Figure 27:
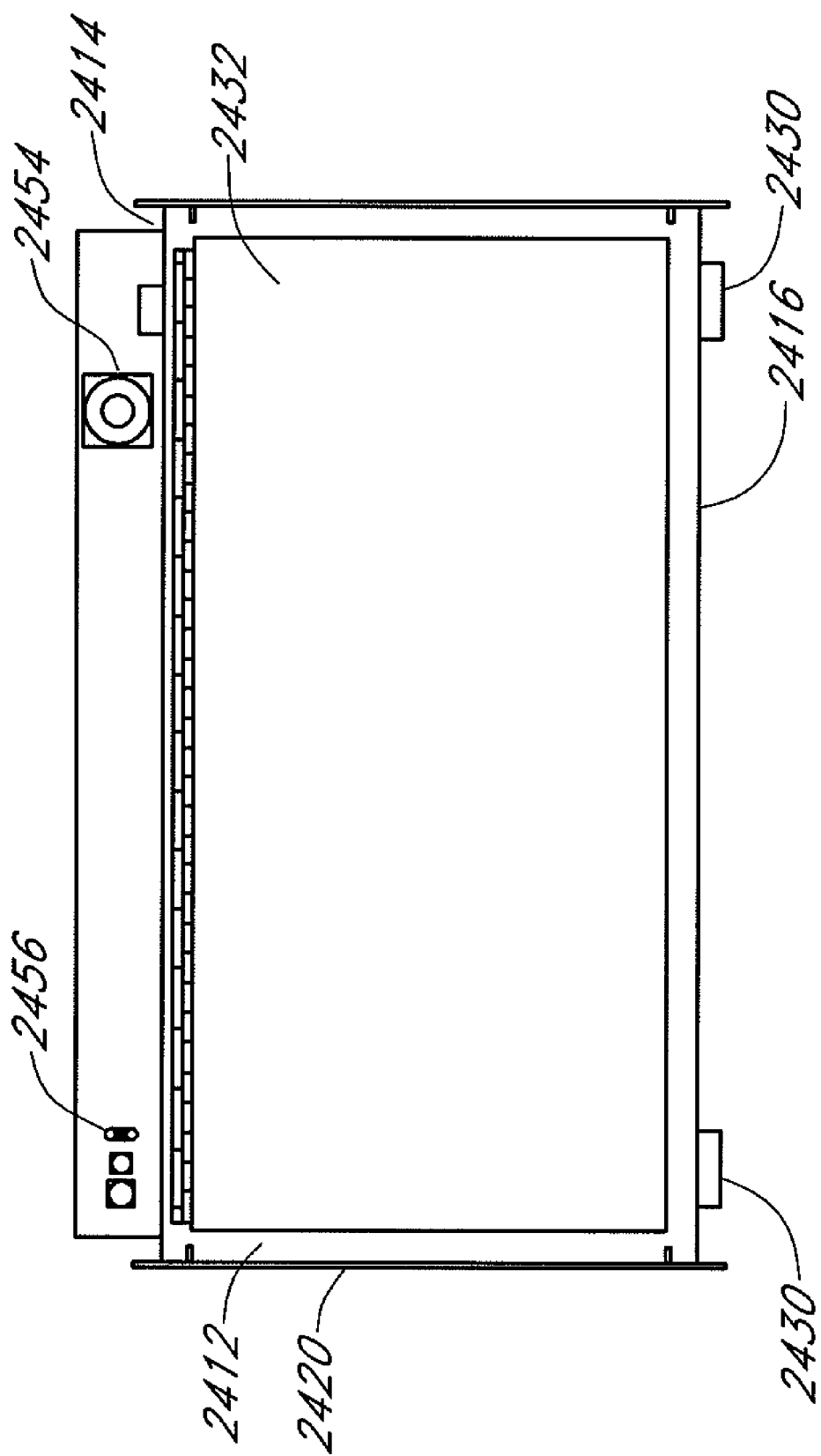
FIG. 27 is a top plan view of the air sterilization chamber of FIG. 23.

FIG. 27 is a top plan view of the air sterilization chamber, in which the hinge 2436 of the access port 2432 can be clearly seen. It will be understood that the hinged access port preferably comprises an airtight interior seal, and so a gasket or a layer of deformable material may be used to provide such a seal when the access port is closed. The upper fan 2454 can also be seen, along with the controls 2456. The other compartments on the exterior of the air sterilization chamber may be accessible via removable panels, hinged panels, or any other suitable method of access.

The air sterilization chamber may be a standalone structure, or may be incorporated into an HVAC or other ventilation system. In certain embodiments, the sterilization chamber may be placed at or near the intake of the ventilation system, so as to provide air sterilization for a large portion or all air drawn into the building. In other embodiments, the sterilization chamber may be placed at or near the end of the ventilation system so as to provide sterilized air for a smaller portion of a building. The system may also be used in conjunction with an exhaust vent so as to sterilize exhaust. It will be understood that aspects of the system such as the size of the sterilization chamber may vary greatly depending on the particular use of the air sterilization chamber.

Specific parts, shapes, materials, functions and modules have been set forth, herein. However, a skilled technologist will realize that there are many ways to fabricate the system of the present invention, and that there are many parts, components, modules or functions that may be substituted for those listed above. While the above detailed description has shown, described, and pointed out the fundamental novel features of the invention as applied to various embodiments, it will be understood that various omissions and substitutions and changes in the form and details of the components illustrated may be made by those skilled in the art, without departing from the spirit or essential characteristics of the invention.

What is claimed is:

1. An UV flux multiplying air sterilization chamber comprising:
   a plurality of inner surfaces, wherein substantially all of said inner surfaces are covered with expanded PTFE, having diffuse reflective behavior above 95%;
   an inlet aperture for air to flow into the chamber and an outlet aperture for air to flow out of said chamber,
   perforated panels overlaying at least part of said inlet aperture and said outlet aperture, wherein the interior surfaces of said perforated panels are coated with a layer of expanded PTFE, and wherein the perforated panels comprise a plurality of panel apertures extending therethrough, the panel apertures having a distribution density which is greater near the edges of the perforated panels than in the center of the perforated panels; and
   a plurality of fixtures located on at least two of said inner surfaces, wherein said plurality of fixtures are covered with a layer of expanded PTFE and are configured to retain a plurality of UV lamps in positions substantially parallel to the air flow between said inlet aperture and said outlet aperture, wherein said fixtures are further configured to retain said plurality of UV lamps in positions substantially parallel to and proximate to the inner surfaces on which they are mounted.

2. The air sterilization chamber of claim 1, wherein a pressure drop within the apparatus is less than about 0.5 w.i.g.

3. The air sterilization chamber of claim 1, wherein the expanded PTFE has a reflectivity which is greater than about 99%.

4. The air sterilization chamber of claim 1, wherein the panel apertures comprise at least one of a slot-shaped aperture or an oval-shaped aperture.

5. The air sterilization chamber of claim 1, wherein a ratio of the sum of the open areas through which light can escape the chamber and light absorbing areas of the chamber to the total surface area of the chamber is represented by a, and a is less than 0.1

6. The air sterilization chamber of claim 1, wherein the total area of the panel apertures in the perforated panels is more than 10% of the total area of the interior surface of the perforated panels.

7. An UV flux multiplying air sterilization chamber comprising:
- a plurality of inner surfaces, wherein at least one of said inner surfaces comprises a reflective material having a diffuse reflective behavior and a reflectivity of greater than about 90%;
- an inlet aperture for air to flow into the chamber and an outlet aperture for air to flow out of said chamber, wherein the inlet and outlet apertures comprise perforated panels overlying at least a portion of said inlet and outlet apertures, the perforated panels comprising a plurality of panel apertures extending therethrough, and wherein a distribution density of the panel apertures in the perforated panels is greater near the edges of the panels than in the center of the panels; and
- a light source emitting an UV light, wherein a flux of said UV light is multiplied by reflecting said UV light multiple times from the inner surfaces of the chamber.

8. The air sterilization chamber of claim 7, wherein the light source comprises at least one UV lamp oriented substantially parallel to the air flow within the chamber.

9. The air sterilization chamber of claim 8, wherein said at least one UV lamp is positioned substantially parallel to and proximate a first interior surface of the chamber.

10. The air sterilization chamber of claim 9, additionally comprising at least one UV lamp positioned substantially parallel to and proximate a second interior surface of the chamber, said second interior surface being substantially opposite the first interior surface.

11. The air sterilization chamber of claim 7, wherein the perforated panels comprise a reflective material located on the interior surfaces of the perforated panels.

12. The air sterilization chamber of claim 11, wherein the reflective material comprises expanded PTFE.

13. The air sterilization chamber of claim 7, wherein the panel apertures have a diameter of about 0.5 to about 2.5 inches.

14. The air sterilization chamber of claim 7, wherein the total area of the panel apertures is between 10% and 25% of the total area of the interior surface of the perforated panels.

15. The air sterilization chamber of claim 7, wherein said light source is positioned inside the chamber.

16. The air sterilization chamber of claim 7, wherein said reflective material has a UV light reflectivity of more than about 94%.

17. The air sterilization chamber of claim 7, wherein said reflective material comprises a mixture of a binder and reflecting additives such as barium sulfate, magnesium fluoride, magnesium oxide or aluminum oxide, holmium oxide, calcium oxide, lanthanum oxide, germanium oxide, tellurium oxide, europium oxide, erbium oxide, neodymium oxide, samarium oxide or ytterbium oxide.

18. The air sterilization chamber of claim 7, wherein the ratio of an area of said panel apertures plus a light absorbing surface area of said light source are less than about 5% of a total inner surface area of the sterilization chamber.

19. The air sterilization chamber of claim 7, further comprising blocking means for limiting escape of light through said inlet aperture and said outlet aperture.

20. The air sterilization chamber of claim 19, wherein the blocking means consists of structures with open and closed spaces.

21. The air sterilization chamber of claim 19, wherein the blocking means comprises more than one surface.

22. The air sterilization chamber of claim 19, wherein the blocking means comprises slats that are separated by open spaces.

23. The air sterilization chamber of claim 22, wherein a surface of the slats facing an inside of the chamber comprise diffuse reflecting material with a reflectivity of greater than 75%.

24. The air sterilization chamber of claim 7, wherein a ratio of the sum of the open areas through which light can escape the chamber and light absorbing areas of the chamber to the total surface area of the sterilization chamber is represented by a, and a is less than 0.1.

25. The air sterilization chamber of claim 7, wherein the panel apertures comprise at least one of a slot-shaped aperture or an oval-shaped aperture.

26. The air sterilization chamber of claim 7, wherein the total area of the panel apertures is more than 10% of the total area of the interior surface of the perforated panels.

27. The air sterilization chamber of claim 7, wherein said reflective material has a UV light reflectivity of more than about 99%.

* * * * *